(12) United States Patent
Burnette

(10) Patent No.: US 9,176,122 B2
(45) Date of Patent: Nov. 3, 2015

(54) BIOMARKERS FOR PREDICTING RESPONSE TO IMMUNOSUPPRESSIVE THERAPY

(75) Inventor: Pearlie K. Burnette, Tampa, FL (US)

(73) Assignees: UNIVERSITY OF SOUTH FLORIDA, Tampa, FL (US); UNITED STATES DEPARTMENT OF VETERANS AFFAIRS, Washington, DC (US)

( * ) Notice: Subject to any disclaimer, the term of this patent is extended or adjusted under 35 U.S.C. 154(b) by 138 days.

(21) Appl. No.: 12/933,975

(22) PCT Filed: Mar. 24, 2009

(86) PCT No.: PCT/US2009/001875
§ 371 (c)(1),
(2), (4) Date: Dec. 7, 2010

(87) PCT Pub. No.: WO2009/120341
PCT Pub. Date: Oct. 1, 2009

(65) Prior Publication Data
US 2011/0091481 A1   Apr. 21, 2011

Related U.S. Application Data

(60) Provisional application No. 61/038,938, filed on Mar. 24, 2008, provisional application No. 61/046,219, filed on Apr. 18, 2008.

(51) Int. Cl.
*A61K 39/00* (2006.01)
*A61K 39/38* (2006.01)
(Continued)

(52) U.S. Cl.
CPC ...... *G01N 33/5094* (2013.01); *G01N 33/57426* (2013.01); *G01N 33/6875* (2013.01);
(Continued)

(58) Field of Classification Search
None
See application file for complete search history.

(56) References Cited

U.S. PATENT DOCUMENTS

2006/0063256 A1   3/2006   Norment et al.
2006/0121021 A1   6/2006   Hunig et al.
2007/0184031 A1   8/2007   Prabhakar et al.

OTHER PUBLICATIONS

Alcover A, Alarcon B. Internalization and intracellular fate of TCR-CD3 complexes. *Crit Rev Immunol.* 2000;20:325-346.

(Continued)

*Primary Examiner* — Michail Belyavskyi
(74) *Attorney, Agent, or Firm* — Saliwanchik, Lloyd & Eisenschenk

(57) ABSTRACT

The subject invention concerns methods and materials for assessing a patient's likelihood of responsiveness to an immunosuppressive therapy. The subject invention is contemplated for use with patients having an autoimmune disorder. In an exemplified embodiment, the methods of the invention are used for assessing and/or treating a patient with MDS. In one embodiment, a method of the invention comprises analyzing T cells of a patient for dysregulation of $CD4^+$ and/or $CD8^+$ T cell subsets, and determining the patient's likelihood of responsiveness to IST based on the level of dysregulation of the patient's $CD4^+$ and/or $CD8^+$ T cell subsets. In one embodiment, an increased likelihood of patient responsiveness to IST is associated with an increased percentage of $CD4^+$ and/or $CD8^+$ effector memory T cells and/or terminal effector memory T cells for a patient. The subject invention also concerns methods for treating a patient with an autoimmune disorder, such as MDS. In one embodiment, a method of the invention comprises determining if a patient is likely to respond to IST, wherein said determination is made using a method of the present invention for assessing likelihood of responsiveness to IST; and if the patient is determined to be one likely to respond to IST, administering an effective regimen of IST to the patient.

32 Claims, 10 Drawing Sheets

(51) Int. Cl.
  *A61K 38/00* (2006.01)
  *G01N 33/50* (2006.01)
  *G01N 33/574* (2006.01)
  *G01N 33/68* (2006.01)

(52) U.S. Cl.
  CPC .............. *G01N2333/70564* (2013.01); *G01N 2333/70589* (2013.01); *G01N 2800/22* (2013.01); *G01N 2800/52* (2013.01)

(56) References Cited

OTHER PUBLICATIONS

Azua-Lieberman N, Markel G, Mizrahi S, et al. The involvement of NK cells in ankylosing spondylitis. *Int Immunol.* 2005;17:837-845.
Bagby GC, Lipton JM, Sloand EM, Schiffer CA. Marrow failure. *Hematology Am Soc Hematol Educ Program.* 2004:318-336.
Bauer S, Groh V, Wu J, et al. Activation of NK cells and T cells by NKG2D, a receptor for stress-inducible MICA. *Science.* 1999;285:727-729.
Bennett JM, Komrokji RS. The myelodysplastic syndromes: diagnosis, molecular biology and risk assessment. *Hematology.* 2005;10 Suppl 1:258-269.
Boissonnas A, Bonduelle O, Lucas B, Debre P, Autran B, Combadiere B. Differential requirement of caspases during naive T cell proliferation. *Eur J Immunol.* 2002;32:3007-3015.
Bonzheim I, Geissinger E, Roth S, et al. Anaplastic large cell lymphomas lack the expression of T-cell receptor molecules or molecules of proximal T-cell receptor signaling. *Blood.* 2004;104:3358-3360.
Bronstein-Sitton N, Cohen-Daniel L, Vaknin I, et al. Sustained exposure to bacterial antigen induces interferon-gamma-dependent T cell receptor zeta down-regulation and impaired T cell function. *Nat Immunol.* 2003;4:957-964.
Bronstein-Sitton N, Wang L, Cohen L, Baniyash M. Expression of the T cell antigen receptor zeta chain following activation is controlled at distinct checkpoints. Implications for cell surface receptor down-modulation and re-expression. *J Biol Chem.* 1999;274:23659-23665.
Castriconi R, Della Chiesa M, Moretta A. Shaping of adaptive immunity by innate interactions. *C R Biol.* 2004;327:533-537.
Champagne P, Ogg GS, King AS, et al. Skewed maturation of memory HIV-specific CD8 T lymphocytes. *Nature.* 2001;410:106-111.
De Rosa SC, Herzenberg LA, Herzenberg LA, Roederer M. 11-color, 13-parameter flow cytometry: identification of human naive T cells by phenotype, function, and T-cell receptor diversity. *Nat Med.* 2001;7:245-248.
Dejaco C, Duftner C, Schirmer M. Are regulatory T-cells linked with aging? *Exp Gerontol.* 2006;41:339-345.
Deryckere D, DeGregori J. E2F1 and E2F2 are differentially required for homeostasis-driven and antigen-induced T cell proliferation in vivo. J Immunol. 2005;175:647-655.
Elisseeva OA, Oka Y, Tsuboi A, et al. Humoral immune responses against Wilms tumor gene WT1 product in patients with hematopoietic malignancies. *Blood.* 2002;99;3272-3279.
Epling-Burnette PK, Bai F. Painter JS, et al. Reduced natural killer (NK) function associated with high-risk myelodysplastic syndrome (MDS) and reduced expression of activating NK receptors. *Blood.* 2007;109:4816-4824.
Epling-Burnette PK, Liu JH, Catlett-Falcone R, et al. Inhibition of STAT3 signaling leads to apoptosis of leukemic large granular lymphocytes and decreased Mcl-1 expression. *J Clin Invest.* 2001;107:351-362.
Epling-Burnette PK, Painter JS, Rollison DE, et al. Prevalence and clinical association of clonal T-cell expansions in Myelodysplastic Syndrome. *Leukemia.* 2007;21:659-667.

Epling-Burnette PK, Zhong B, Bai F. et al. Cooperative regulation of Mcl-1 by Janus kinase/stat and phosphatidylinositol 3-kinase contribute to granulocyte-macrophage colony-stimulating factor-delayed apoptosis in human neutrophils. *J Immunol.* 2001;166:7486-7495.
Ferrandina G, Ranelletti FO, Legge F, et al. Celecoxib up-regulates the expression of the zeta chain of T cell receptor complex in tumor-infiltrating lymphocytes in human cervical cancer. *Clin Cancer Res.* 2006;12:2055-2060.
Gilhar A, Ullmann Y, Kerner H, et al. Psoriasis is mediated by a cutaneous defect triggered by activated immunocytes: induction of psoriasis by cells with natural killer receptors. *J Invest Dermatol.* 2002;119:384-391.
Goldrath AW, Bevan MJ. Selecting and maintaining a diverse T-cell repertoire. *Nature.* 1999;402:255-262.
Goronzy JJ, Henel G, Sawai H, et al. Costimulatory pathways in rheumatoid synovitis and T-cell senescence. *Ann N Y Acad Sci.* 2005;1062:182-194.
Goronzy JJ, Weyand CM. Rheumatoid arthritis. *Immunol Rev.* 2005;204:55-73.
Goronzy JJ, Weyand CM. Thymic function and peripheral T-cell homeostasis in rheumatoid arthritis. *Trends Immunol.* 2001;22:251-2
Greenberg P, Cox C, LeBeau MM, et al. International scoring system for evaluating prognosis in myelodysplastic syndromes. *Blood.* 1997;89:2079-2088.
Hazenberg MD, Otto SA, Cohen Stuart JW, et al. Increased cell division but not thymic dysfunction rapidly affects the T-cell receptor excision circle content of the naive T cell population in HIV-1 infection. *Nat Med.* 2000;6:1036-1042.
Hazenberg MD, Stuart JW, Otto SA, et al. T-cell division in human immunodeficiency virus (HIV)-1 infection is mainly due to immune activation: a longitudinal analysis in patients before and during highly active antiretroviral therapy (HAART). *Blood.* 2000;95:249-255.
Healy CG, Simons JW, Carducci MA, et al. Impaired expression and function of signal-transducing zeta chains in peripheral T cells and natural killer cells in patients with prostate cancer. *Cytometry.* 1998;32:109-119.
Henel G, Singh K, Cui D. et al. Uncoupling of T-cell effector functions by inhibitory killer immunoglobulin-like receptors. *Blood.* 2006;107:4449-4457.
Kochenderfer JN, Kobayashi S, Wieder ED, Su C, Molldrem JJ. Loss of T-lymphocyte clonal dominance in patients with myelodysplastic syndrome responsive to immunosuppression. *Blood.* 2002;100:3639-3645.
Kook H, Zeng W, Guibin C. Kirby M, Young NS, Maciejewski JP. Increased cytotoxic T cells with effector phenotype in aplastic anemia and myelodysplasia. *Exp Hematol.* 2001;29:1270-1277.
Kordasti SY, Ingram W, Hayden J, et al. CD4+CD25high Foxp3+ regulatory T-cells in Myelodysplastic Syndrome (MDS). *Blood.* 2007;110:847-850.
Lim Zy, Killick S, Germing U, et al. Low IPSS score and bone marrow hypocellularity in MDS patients predict hematological responses to antithymocyte globulin. *Leukemia.* 2007;21:1436-1441.
Makarenkova VP, Bonsai V, Matta BM, Perez LA, Ochoa JB. CD11b+/Gr-1+ myeloid suppressor cells cause T cell dysfunction after traumatic stress. *J Immunol.* 2006;176:2085-2094.
Maldonado A, Mueller YM, Thomas P. Bojczuk P. O'Connors C. Katsikis PD. Decreased effector memory CD45RA+ CD62L− CD8+ T cells and increased central memory CD45RA-CD62L+ CD8+ T cells in peripheral blood of rheumatoid arthritis patients. *Arthritis Res Ther.* 2003;5:R91-96.
Martin MP, Nelson G, Lee JH, et al. Cutting edge: susceptibility to psoriatic arthritis: influence of activating killer Ig-like receptor genes in the absence of specific HLA-C alleles. *J Immunol.* 2002;169:2818-2822.
Molldrem JJ, Jiang YZ, Stetler-Stevenson M, Mavroudis D, Hensel N, Barrett AJ. Haematological response of patients with myelodysplastic syndrome to antithymocyte globulin is associated with a loss of lymphocyte-mediated inhibition of CFU-GM and alterations in T-cell receptor Vbeta profiles. *Br J Haematol.* 1998;102:1314-1322.

(56) References Cited

OTHER PUBLICATIONS

Nakajima H, Kawasaki K, Oka Y, et al. WT1 peptide vaccination combined with BCG-CWS is more efficient for tumor eradication than WT1 peptide vaccination alone. *Cancer Immunol Immunother.* 2004;53:617-624.

Naylor K, Li G, Vallejo AN, et al. The influence of age on T cell generation and TCR diversity. *J Immunol.* 2005;174:7446-7452.

Oka Y, Tsuboi A, Murakami M, et al. Wilms tumor gene peptide-based immunotherapy for patients with overt leukemia from myelodysplastic syndrome (MDS) or MDS with myelofibrosis. *Int J Hematol.* 2003;78:56-61.

Okamoto T, Okada M, Mori A, et al. Correlation between immunological abnormalities and prognosis in myelodysplastic syndrome patients. *Int J Hematol.* 1997;66:345-351.

Otsuji M, Kimura Y, Aoe T, Okamoto Y, Saito T. Oxidative stress by tumor-derived macrophages suppresses the expression of CD3 zeta chain of T-cell receptor complex and antigen-specific T-cell responses. *Proc Natl Acad Sci U S A.* 1996;93:13119-13124.

Rabin RL, Roederer M, Maldonado Y, Petru A, Herzenberg LA, Herzenberg LA. Altered representation of naive and memory CD8 T cell subsets in HIV-infected children. *J Clin Invest.* 1995;95:2054-2060.

Rajagopalan S, Long EO. Understanding how combinations of HLA and KIR genes influence disease. *J Exp Med.* 2005;201:1025-1029.

Rodriguez PC, Zea AH, DeSalvo J, et al. L-arginine consumption by macrophages modulates the expression of CD3 zeta chain in T lymphocytes. *J lmmunol.* 2003;171:1232-1239.

Rollison, D. E. Epidemiologic studies of polyomaviruses and cancer: previous findings, methodologic challenges and future directions. *Adv Exp Med Biol.* 2006;577:342.

Sakaguchi S, Sakaguchi N, Shimizu J, et al. Immunologic tolerance maintained by CD25+ CD4+ regulatory T cells: their common role in controlling autoimmunity, tumor immunity, and transplantation tolerance. *Immunol Rev.* 2001;182:18-32.

Sallusto F, Lenig D, Forster R, Lipp M, Lanzavecchia A. Two subsets of memory T lymphocytes with distinct homing potentials and effector functions. *Nature.* 1999;401:708-712.

San Jose E, Borroto A, Niedergang F, Alcover A, Alarcon B. Triggering the TCR complex causes the downregulation of nonengaged receptors by a signal transduction-dependent mechanism. *Immunity.* 2000;12:161-170.

Santin I, de Nanclares GP, Calvo B, Gaafar A, Castano L, Bilbao JR. Killer cell immunoglobulin-like receptor (KIR) genes in the Basque population: association study of KIR gene contents with type 1 diabetes mellitus. *Hum Immunol.* 2006;67:118-124.

Santner-Nanan B, Seddiki N, Zhu E, et al. Accelerated age-dependent transition of human regulatory T cells to effector memory phenotype. *Int Immunol.* 2008;20(3):375-383.

Saunthararajah Y, Molldrem JL, Rivera M, et al. Coincident myelodysplastic syndrome and T-cell large granular lymphocytic disease: clinical and pathophysiological features. *Br J Haematol.* 2001;112:195-200.

Saunthararajah Y, Nakamura R, Nam JM, et al. HLA-DR15 (DR2) is overrepresented in myelodysplastic syndrome and aplastic anemia and predicts a response to immunosuppression in myelodysplastic syndrome. *Blood.* 2002;100:1570-1574.

Saunthararajah Y, Nakamura R, Wesley R, Wang QJ, Barrett AJ. A simple method to predict response to immunosuppressive therapy in patients with myelodysplastic syndrome. *Blood.* 2003;102:3025-3027.

Schwab R, Szabo P, Manavalan JS, et al. Expanded CD4+ and CD8+ T cell clones in elderly humans. *J Immunol.* 1997;158:4493-4499.

Shen S, Ding Y, Tadokoro CE, et al. Control of homeostatic proliferation by regulatory T cells. *J Clin Invest.* 2005;115:3517-3526.

Sloand EM, Mainwaring L, Fuhrer M, et al. Preferential suppression of trisomy 8 compared with normal hematopoietic cell growth by autologous lymphocytes in patients with trisomy 8 myelodysplastic syndrome. *Blood.* 2005;106:841-851.

Sokol RJ, Hewitt S, Booker DJ. Erythrocyte autoantibodies, autoimmune haemolysis, and myelodysplastic syndromes. *J Clin Pathol.* 1989;42:1088-1091.

Stadler M, Germing U, Kliche KO, et al. A prospective, randomised, phase II study of horse antithymocyte globulin vs rabbit antithymocyte globulin as immune-modulating therapy in patients with low-risk myelodysplastic syndromes. *Leukemia.* 2004;18:460-46.

Sun, M., J. Zhang, S. Liu, Y. Liu, and D. Zheng. Sp1 is involved in 8-chloro-adenosine-upregulated death receptor 5 expression in human hepatoma cells. *Oncol Rep.* 2008;19:177.

Taylor DD, Gercel-Taylor C, Lyons KS, Stanson J, Whiteside TL. T-cell apoptosis and suppression of T-cell receptor/CD3-zeta by Fas ligand-containing membrane vesicles shed from ovarian tumors. *Clin Cancer Res.* 2003;9:5113-5119.

Valmori D, Merlo A, Souleimanian NE, Hesdorffer CS, Ayyoub M. A peripheral circulating compartment of natural naive CD4 Tregs. *J Clin Invest.* 2005;115:1953-1962.

Van Der Slik AR, Koeleman BP, Verduijn W, Bruining GJ, Roep BO, Giphart MJ. KIR in Type 1 Diabetes: Disparate Distribution of Activating and Inhibitory Natural Killer Cell Receptors in Patients Versus HLA-Matched Control Subjects. *Diabetes.* 2003;52:2639-2642.

Voulgarelis M. Giannouli S, Ritis K, Tzioufas AG. Myelodysplasia-associated autoimmunity: clinical and pathophysiologic concepts. *Eur J Clin Invest.* 2004;34:690-700.

Wang HQ, Shao ZH, Shi J. et al. Burden of abnormal hematopoietic clone in patients with myelodysplastic syndromes. *Chin Med Sci J.* 2006;21:99-103.

Warrington KJ, Takemura S. Goronzy JJ, Weyand CM. CD4+,CD28— T cells in rheumatoid arthritis patients combine features of the innate and adaptive immune systems. *Arthritis Rheum.* 2001;44:13-20.

Weyand CM, Goronzy JJ. T-cell responses in rheumatoid arthritis: systemic abnormalities-local disease. *Curr Opin Rheumatol.* 1999;11:210-217.

Whiteside TL. Down-regulation of zeta-chain expression in T cells: a biomarker of prognosis in cancer? *Cancer Immunol Immunother.* 2004;53:865-878.

Young NS, Abkowitz JL, Luzzatto L. New Insights into the Pathophysiology of Acquired Cytopenias. *Hematology (Am Soc Hematol Educ Program).* 2000:18-38.

Young, N. S. Immunosuppressive treatment of acquired aplastic anemia and immune-mediated bone marrow failure syndromes. *Int J Hematol.* 2002;75:129.

Hiura, T. et al. Both regulatory T cells and antitumor effector T cells are primed in the same draining lymph nodes during tumor progression *J. Immunol.*, 2005;175:5058-5066.

Bulwin, G-C. et al. TIRC7 inhibits T cell proliferation by modulation of CTLA-4 expression *J. Immunol.*, 2006;177:6833-6841.

Yamashita, K. et al. Severe chronic graft-versus-host disease is characterized by a preponderance of CD4+ effector memory cells relative to central memory cells *Blood*, 2004;103:3986-3988.

Jädersten M and E. Hellström-Lindberg E, "Myelodysplastic syndromes: biology and treatment" *Journal of Internal Medicine*, 2008, 265:307-328.

Madkaikar M and Ghosh K, "Treating patients of myelodysplastic syndrome with antithymocytic globulin—should we be more selective?" *Blood*, 2003, 102(10):3851-3852.

Steensma DP et al., "Antithymocyte globulin has limited efficacy and substantial toxicity in unselected anemic patients with myelodysplastic syndrome" *Blood*, 2003, 101(6):2156-2158.

Sugimori C and Epling-Burnette PK, "Immune dysregulation in myelodysplastic syndrome" *Hematology Reports*, 2010, 2:e1.

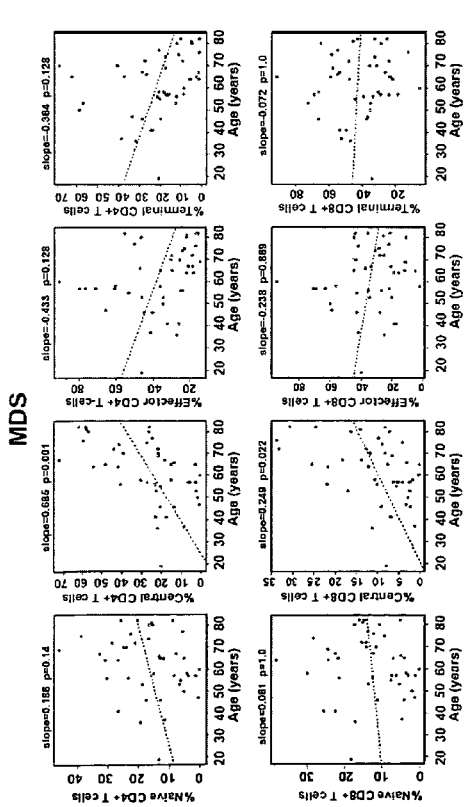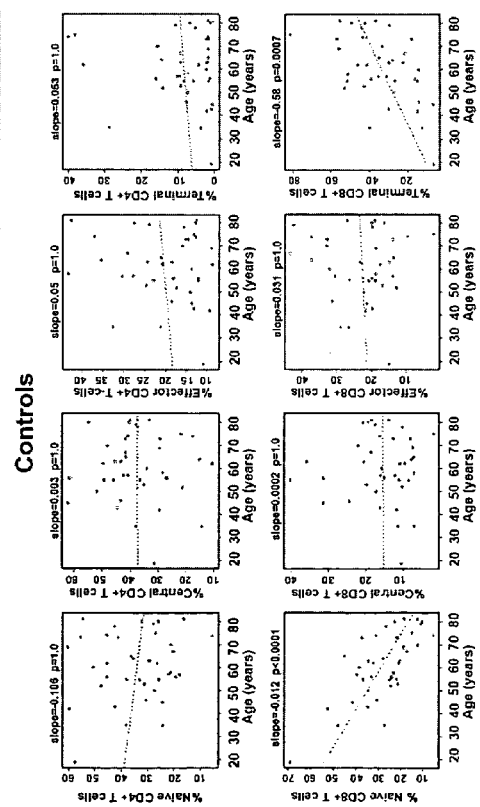

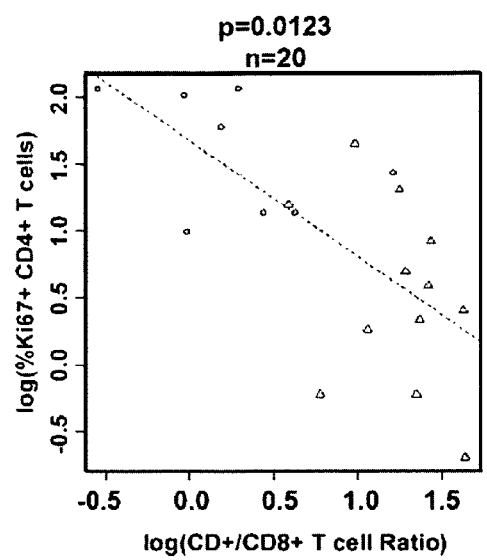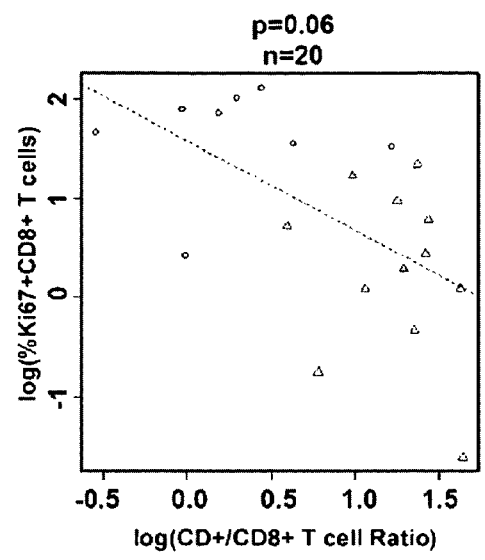
FIG. 4C-1              FIG. 4C-2

BIOMARKERS FOR PREDICTING RESPONSE TO IMMUNOSUPPRESSIVE THERAPY

CROSS-REFERENCE TO RELATED APPLICATIONS

The present application is the National Stage of International Application Number PCT/US2009/001875, filed Mar. 24, 2009, which claims the benefit of U.S. Provisional Application Ser. No. 61/038,938, filed Mar. 24, 2008 and U.S. Provisional Application Ser. No. 61/046,219, filed Apr. 18, 2008, each of which is hereby incorporated by reference herein in its entirety, including any figures, tables, nucleic acid sequences, amino acid sequences, and drawings.

GOVERNMENT SUPPORT

This invention was made with government support under grant number CA11212 awarded by the National Institutes of Health. The government has certain rights in the invention.

BACKGROUND OF THE INVENTION

Myelodysplastic syndromes (MDS) are acquired clonal disorders of hematopoietic progenitors that are characterized by peripheral cytopenias and cytologic dysplasias (Greenberg et al., 1997). There is a strong association between bone marrow failure and autoimmunity that transects classical autoimmune processes such as aplastic anemia, rheumatoid arthritis, Felty's Syndrome, and large granular lymphocyte (LGL) leukemia (Colmegna et al., 2008; Loughran, Jr., 1998; Starkebaum et al., 1997). Similar to these quintessential autoimmune bone marrow failure syndromes, hematopoietic suppression by a T-cell dominant autoimmune process and IST responsiveness has been proposed in younger MDS patients. In MDS cases where hematologic improvement is observed after IST, the response can be durable leading to improved long-term survival (Lim et al., 2007; Molldrem et al., 1997; Biesma et al., 1997). Despite a clear therapeutic benefit and a basic understanding of immune pathology, IST is rarely offered to MDS patients as a treatment option in the United States due to an uncertainty about the appropriate selection of patients for such therapy (Steensma & Tefferi, 2003). There is an underlying concern that inappropriate use of IST may negatively impact risk for leukemia progression, which occurs in 30-40% of MDS cases. This is of particular concern in younger patients that may benefit from allogeneic stem cell transplantation (List et al., 2004). The identification of immunological factors in addition to younger age to guide appropriate selection of patients for IST based on immune pathobiology is critical to the optimization of MDS treatment.

In MDS patients of younger age, a higher frequency of clinical responsiveness to immunosuppressive therapy (IST) with anti-thymocyte globulin (ATG) and/or cyclosporine-A (CyA) suggests that unique immune pathobiology contributes to the refractory cytopenias observed in such patients. Factors associated with response to IST included HLA-DR-15 genotype, age, <5% marrow blasts, low risk for leukemia transformation and in some studies hypocellularity (Lim et al., 2007; Sun et al., 2008). Among these factors, younger age is the most consistently linked clinical feature associated with IST responsiveness in both patients with aplastic anemia and in patients with MDS (Sun et al., 2008; Young, 2002). A model of immune pathogenesis first proposed by Molldrem et al suggests that unique or overexpressed antigens stimulate CD8+ T-cells, induce T-cell receptor (TCR) repertoire contraction through expansion of memory cells, and repress hematopoiesis through cross-reactive antigens expressed on normal bone marrow progenitors (Molldrem et al., 1998). In the subset of patients responsive to immunosuppression, effects of the self-reactive T-cell populations are thought to be eliminated by the immunosuppressive actions of these drugs (Molldrem et al., 1998; Kochenderfer et al., 2002).

BRIEF SUMMARY OF THE INVENTION

The subject invention concerns methods and materials for assessing a patient's likelihood of responsiveness to an immunosuppressive therapy. The subject invention is contemplated for use with patients having an autoimmune disorder. In an exemplified embodiment, the methods of the invention are used for assessing and/or treating a patient with MDS. In one embodiment, a method of the invention comprises analyzing T cells of a patient for dysregulation of $CD4^+$ and/or $CD8^+$ T cell subsets, and determining the patient's likelihood of responsiveness to IST based on the level of dysregulation of the patient's $CD4^+$ and/or $CD8^+$ T cell subsets. In a specific embodiment, an increased likelihood of patient responsiveness to IST is associated with an increased percentage of $CD4^+$ and/or $CD8^+$ effector memory T cells and/or terminal effector memory T cells for a patient.

The subject invention also concerns methods for treating a patient with an autoimmune disorder, such as MDS. In one embodiment, a method of the invention comprises determining if a patient is likely to respond to IST, wherein said determination is made using a method of the present invention for assessing likelihood of responsiveness to IST; and if the patient is determined to be one likely to respond to IST, administering an effective regimen of IST to the patient.

BRIEF DESCRIPTION OF THE DRAWINGS

In FIG. 1A, a multivariable regression analysis was performed with the log-transformed ratio of CD4:CD8 as the dependent variable and age and disease status (MDS v normal control) as independent variables (MDS=open circles and Control=open triangle). An interaction term between age and disease status was not statistically significant (p-value=0.71) and was dropped from the final model. Disease status was significantly associated with log(CD4:CD8) (p-value<0.0001) while adjusting for age. Regression analyses were also performed separately for CD4 (FIG. 1B) and CD8 (FIG. 1C) in a log scale. While adjusting for age, % CD4 was significantly lower in MDS cases compared to controls (p-value<0.0001) but there was no difference in % CD8 (p-value=0.42). No interaction between age and disease status was observed in either model (p=0.31 and p=0.13 for CD4 and CD8, respectively).

FIGS. 3A and 3B show age-dependent changes in naïve and memory T-cell subpopulations in MDS patients. Using CD45RA and CD62L staining, naïve CD62L+/CD45RA+ (naïve), central memory CD62L+/CD45RA− (central), effector memory CD62L−/CD45RA+ (effector), and terminal effector memory CD62L−/CD45RA+ (terminal) were determined in 47 MDS patients (black circles, dotted line) and plotted against age in years. The frequency of CD4+ and CD8+ T-cell subpopulations is shown in MDS patients (FIG. 3A) and controls (FIG. 3B). Associations with age were evaluated using simple linear regression, adjusting for multiple testing with the Holm step down method. Lines indicate data trends in MDS cases and controls, and the slopes with corresponding p-values are presented (p-values<0.05 are considered statistically significant).

FIGS. 4A-4C show the change in phenotype and T-cell homeostasis after IST. In FIG. 4A, the CD4:CD8 ratio was calculated and compared between responders and non-responders before treatment with anti-Thymocyte globulin immunosuppression (ATG) or ATG in combination with CyA (ATG+CyA). In FIGS. 4B-1 and 4B-2, homeostatic proliferation was determined by Ki-67 expression (% Ki-67 positive) in CD4+ (FIG. 4B-1) and CD8+ (FIG. 4B-2) (first gated on CD3+ T-cells) and results were compared between responders (open dots) and non-responders (open triangle). Associations % Ki-67+/CD4+ (FIG. 4C-1) and % Ki-67+/CD8+ (FIG. 4C-2) T-cells and the CD4:CD8 ratio were evaluated in all patients combined using regression of the log CD4:CD8 ratio vs the Ki-67%/CD4+ and CD8+ adjusted for age. Lines indicate data trends and the corresponding p-values are presented (p-values<0.05 are considered statistically significant).

In FIG. 5A, using expression patterns of CD62L (x-axis) and CD45RA (y-axis), the following populations were distinguished in CD4+ and CD8+ T-cells: naive CD62L+/CD45RA+ (R4), central memory CD62L+/CD45RA– (R5), effector memory CD62L–/CD45RA– (R6), and terminal effector memory CD62L–/CD45RA+ (R7). The % Ki-67 positive cells and isotype control-PE were concomitantly determined on R4-R7 gated populations as shown. Results are shown for the percentage of each subpopulation that expressed Ki-67 was determined in individual gates before and after treatment in one exemplary MDS patient. In FIG. 5B, the % Ki-67 positive CD4+ (solid lines) and CD8+ (dashed lines) were determined in naive CD45RA+/CD62L+ (circle), central memory (CD45RA+/CD62L–) (square), effector memory (triangle), and terminal effector memory (hashed mark). For each of these eight cell populations, changes in % Ki-67 from before treatment (pre-TX) to after treatment (post-TX) were compared between responders (open circles) and non-responders (open triangles) using the Wilcoxon rank sum test, adjusting for multiple testing using the Holm step down method (p<0.05 for all eight comparisons). In FIG. 5C, the pre-TX versus post-TX changes in percentage of naive CD62L+/CD45RA+ were also compared between patients that displayed a clinical response (responders) and patients that failed to respond to immunosuppression (non-responders) using the Wilcoxon rank sum test, adjusting for multiple testing using the Holm step down method.

DETAILED DESCRIPTION OF THE INVENTION

Figure 1A:
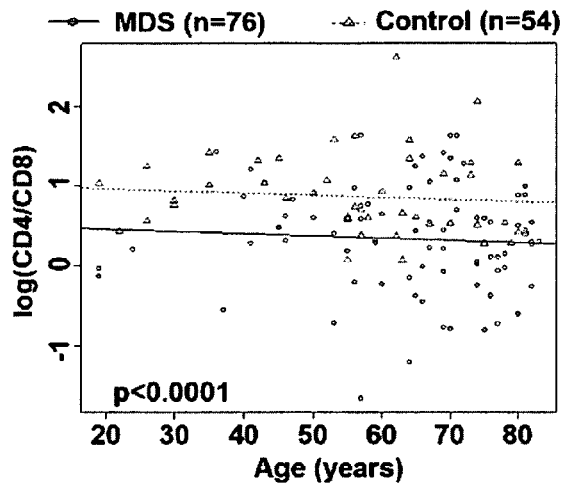
FIGS. 1A-1C shows the ratio of CD4:CD8 T-cells.

The subject invention concerns methods for assessing or predicting a patient's likelihood of responsiveness to an immunosuppressive therapy. The subject invention is contemplated for use with patients having an autoimmune disorder. In an exemplified embodiment, the methods of the invention are used for assessing and/or treating a patient with MDS. In one embodiment, a method of the invention comprises analyzing T cells of a patient for dysregulation of $CD4^+$ and/or $CD8^+$ T cell subsets, and determining the patient's likelihood of responsiveness to IST based on the level of dysregulation of the patient's $CD4^+$ and/or $CD8^+$ T cell subsets. The cells of a patient can be obtained from any suitable biological sample, such as a blood sample. In one embodiment, the blood sample is a peripheral blood sample. The samples can be enriched for lymphocytes, including T cells, using standard methods known in the art. Increases or decreases in percentage of cells, or increases or decreases in percentage of cells expressing a marker protein or nucleic acid of the invention, or increases or decreases in proliferation of cells can be compared to a control sample or to a value obtained from a control sample of patients having the same disorder. For example, in certain embodiments, the control is a value obtained from a sample of patients having the same disorder as the patient that has been determined to be non-responders to IST.

In one embodiment, an increased likelihood of patient responsiveness to IST is associated with an increased percentage of $CD4^+$ and/or $CD8^+$ effector memory T cells and/or terminal effector memory T cells for a patient. In one embodiment, an increased likelihood of responsiveness to IST is associated with an increased percentage of $CD4^+$ effector memory T cells. In a specific embodiment, an increased likelihood of responsiveness to IST is associated with an increased percentage of $CD62L^-$ $CD4^+$ T cells and/or $CD62L^-$ $CD8^+$ T cells for the patient. In a more specific embodiment, an increased likelihood of responsiveness to IST is associated with an increased percentage of $CD62L^-$/$CD45RA^-$ $CD4^+$ T cells for the patient having the disorder.

In a further embodiment, an increased likelihood of patient responsiveness to IST is associated with a decreased percentage of $CD4^+$ and/or $CD8^+$ naive T cells and/or CD4+ and/or $CD8^+$ central memory T cells for a patient. In one embodiment, an increased likelihood of patient responsiveness to IST is associated with a decreased percentage of $CD4^+$ and/or $CD8^+$ central memory T cells for a patient. In a specific embodiment, an increased likelihood of responsiveness to IST is associated with a decreased percentage of $CD62L^+$ $CD4^+$ T cells and/or $CD62L^+$ $CD8^+$ T cells for the patient. In a more specific embodiment, an increased likelihood of responsiveness to IST is associated with a decreased percentage of $CD62L^+/CD45RA^-$ $CD4^+$ and/or $CD62L^+/CD45RA^-$ $CD8^+$ T cells for the patient having the disorder.

In another embodiment, a method of the invention comprises analyzing the level of $CD4^+$ T cells present in the patient, wherein a reduced level of $CD4^+$ T cells is associated with an increased likelihood of IST responsiveness for the patient. In a still further embodiment, a method of the invention further comprises analyzing the ratio of $CD4^+$ to $CD8^+$ T cells ($CD4^+:CD8^+$) in a patient, wherein a lower ratio of $CD4^+:CD8^+$ T cells is associated with an increased likelihood of the patient responding to IST.

In a further embodiment, a method of the invention comprises analyzing the proliferation (e.g., proliferative index) of $CD4^+$ and/or $CD8^+$ T cells of a patient, wherein an increased or higher level of proliferation of $CD4^+$ and/or $CD8^+$ T cells in a patient is associated with an increased likelihood of the patient responding to IST. In a specific embodiment, a method of the invention comprises analyzing the percentage of $Ki-67^+$ $CD4^+$ T cells and/or $Ki-67^+$ $CD8^+$ T cells, wherein an increased percentage of $Ki-67^+$ $CD4^+$ T cells and/or $Ki-67^+$ $CD8^+$ T cells is associated with an increased likelihood of the patient responding positively to IST.

In one embodiment of the methods of the invention, marker proteins are detected and/or quantitated by contacting a biological sample with an antibody or other moiety that binds specifically to a target marker protein, and detecting the presence of a complex of the antibody or binding moiety bound to the target marker protein.

The expression levels of markers, such as CD3; CD4; CD8; CD25; protein target bound by Ki-67 antibody (Genbank accession numbers X74107; NM_001145966; and NM_002417); L-selectin (e.g., CD62L) (Genbank accession number NM_000655); and/or tyrosine phosphatase (e.g., CD45) (Genbank accession numbers NM_080922 and NG_007730), in T cells can be detected using antibodies or aptamers that bind specifically to a target marker protein, or using nucleic acid, such as oligonucleotides, that hybridize with nucleic acid sequences (e.g., mRNA) expressed by genes encoding or associated with the marker protein. An aptamer is an oligonucleotide or peptide molecule that can bind specifically to a target molecule. Aptamers can be prepared from large random pools of oligonucleotides or peptides (Berezovski et al., 2008; Ellington and Szostak, 1990; Hoppe-Seyler and Butz, 2000; Klussmann, 2006). Methods and materials for detecting and/or quantifying expression levels of target nucleic acids are well known in the art and include, for example, Northern blotting and polymerase chain reaction (PCR) methods.

An antibody, or an antibody fragment, or an aptamer that binds specifically to any one of CD3, CD4, CD8, CD25, nuclear or cellular proliferation antigens, L-selectin, and tyrosine phosphatase can be used in the embodiments of the invention. Antibodies or aptamers specific to L-selectin include an antibody or aptamer to the CD62L marker. Antibodies or aptamers specific to tyrosine phosphatase include an antibody or aptamer to one of the CD45RA, CD45RB, and CD45RO markers. An antibody, or antibody fragment, or aptamer that is specific for a cell proliferation antigen can be used in the embodiments of the invention. Antibodies or aptamers specific to a proliferation-associated antigen that can be used according to the present invention include antibodies or aptamers to Ki-67, a nuclear proliferation-associated antigen. In one embodiment, a method of the invention comprises the use of flow cytometry instruments and methods to detect the binding of antibodies or aptamers to antigens on the surface of cells. Flow cytometry instruments and methods of use are well known in the art (Jaroszeski and Heller, 1998; Ormerod, 2008; Radbruch, 2000; Recktenwald and Radbruch, 1997; Shapiro, 2003).

In one aspect, the present invention contemplates the use of nucleic acids as agents for detecting marker proteins in biological samples of patients, wherein the nucleic acids are labeled with a detectable label. The nucleic agents may be labeled with a radioactive label, a fluorescent label, a quantum dot, an enzyme, a chemiluminescent tag, a colorimetric tag or other labels or tags that are discussed above or that are known in the art.

In another aspect, the present invention contemplates the use of Northern blot analysis to detect the presence of marker protein mRNA in a biological sample. The first step of the analysis involves separating a sample containing nucleic acid by gel electrophoresis. The dispersed nucleic acids are then transferred to a nitrocellulose filter or another filter. Subsequently, the filter is contacted with labeled oligonucleotide under suitable hybridizing conditions, e.g., 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of a particular nucleic acid present in the biological fluid of a patient.

Dot blotting involves applying samples that may contain a nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261. Radioimmunoassays, Western blotting, and enzyme linked immunosorbent assay (ELISA) can also be used to detect and quantify marker proteins in a biological sample. RIA, Western blotting, and ELISA methods are well known in the art (Ausubel et al., 1994).

In another aspect, the present invention contemplates the use of polymerase chain reaction (PCR) to detect the presence and/or quantity of a nucleic acid encoding or associated with a marker protein in a biological sample. Polymerase chain reaction is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. PCR is routinely used to detect the presence of a desired sequence (U.S. Pat. No. 4,683,195).

A specific example of PCR that is routinely performed by the skilled artisan to detect desired sequences is reverse transcription PCR (RT-PCR; Saiki et al. (1985) and Scharf et al. (1986)). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan. The amount of a target nucleic acid sequence in a sample can be quantitated using standard PCR methods.

Oligonucleotide primers and probes can be used in PCR methods and other methods involving nucleic acid amplification. In one embodiment, a probe or primer can hybridize to a target polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the target polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention.

In one embodiment of a method of the present invention, the IST that is considered for administration to the patient if the patient is determined to be likely to respond to the IST can be anti-thymocyte globulin (ATG) therapy. In another embodiment, the IST that is considered for administration to the patient if the patient is determined to be likely to respond to the IST can be cyclosporine A (CyA) therapy. In a still further embodiment, the IST that is considered to be administered to a patient is both ATG and CyA therapy. Other IST contemplated by the subject invention include, but is not limited to, use of antibodies to T cell receptors (anti-CD3) and/or IL-2 receptors (anti-CD25); use of interferons; use of Tacrolimus (PROGRAF); use of glucocorticoids; and use of cytostatic compounds such as alkylating agents, methotrexate, and azathioprine.

The subject invention also concerns methods for treating a patient having an autoimmune disorder, such as MDS, comprising the steps of determining if a patient is likely to respond to IST, wherein said determination is made using a method of the present invention for assessing likelihood of responsiveness to IST; and if the patient is determined to be one likely to respond to IST, administering an effective regimen of IST to the patient. In one embodiment, the IST administered is anti-thymocyte globulin (ATG) therapy. In another embodiment, the IST administered is cyclosporine A (CyA) therapy. In a still further embodiment, the IST to be administered to a patient is both ATG and CyA therapy. Any other immunosuppressive therapies useful in treating the disorder afflicting the patient are also contemplated within the scope of the invention. In one embodiment, the method further comprises a first step of identifying and/or diagnosing that the patient has or is developing an autoimmune disorder, such as MDS.

Methods of the present invention can also be combined with any other methods or markers known in the art for determining or assessing likelihood of responsiveness to IST for a patient having an autoimmune disorder, such as MDS. For example, wherein the methods are used to assess an MDS patient, the methods of the invention can also incorporate methods utilizing factors such as patient age, HLA-DR2 antigen status of the patient, and/or duration of red cell transfusion dependence (RCTD) (Saunthararajah et al., 2002 and 2003).

The methods of the invention can be used for assessing responsiveness to IST and for treating patients having an autoimmune disorder and/or a disorder in which one of the pathologies is an immune system that is underregulated, or that is overactive, or that is reactive against self, i.e., that recognizes as foreign and mounts an immune response against the patient's own antigens, cells, and tissues. Autoimmune disorders contemplated within the scope of the invention include, but are not limited to, Addison's disease, Crohn's disease, dermatomyositis, diabetes mellitus type 1, Graves' disease, lupus erythematosus, multiple sclerosis (MS), myasthenia gravis, pernicious anemia, polymyositis, rheumatoid arthritis, Sjögren's syndrome, ulcerative colitis, vasculitis, and Wegener's granulomatosis. In an exemplified embodiment, the disorder is MDS.

The subject invention also concerns kits comprising reagents for practicing the methods of the present invention. In one embodiment, a kit of the invention comprises in one or more containers:

i) a reagent for assessing the presence of and/or quantifying the amount of CD4$^+$ T cells in a sample; and/or ii) a reagent for assessing the presence of and/or quantifying the amount of CD8$^+$ T cells in a sample; and/or iii) a reagent for assessing the presence of and/or quantifying the amount of naïve, central memory, effector memory, and/or terminal effector memory T cells in a sample; and/or iv) a reagent for assessing the proliferation of CD4$^+$ and/or CD8$^+$ T cells in a sample.

In one embodiment, a kit of the invention further comprises positive or negative controls or standards that the assayed sample can be compared to. In one embodiment, the kit comprises one or more antibody, an antibody fragment, or aptamer specific to CD4$^+$ or CD8$^+$ T cells. In one embodiment, the kit comprises one or more antibody, antibody fragment, or aptamer specific to CD3 or CD25 markers. In a further embodiment, the kit comprises one or more antibody, an antibody fragment, or aptamer that bind specifically to an L-selectin antigen determinant, such as CD62L and/or one or more antibodies that bind to a tyrosine phosphatase antigen determinant, such as CD45RA, CD45RB, or CD45RO. In another embodiment, the kit comprises one or more antibody, an antibody fragment, or aptamer that bind specifically to Ki-67, a nuclear proliferation-associated antigen. A kit of the invention can comprise any and all of the above embodiments. In another embodiment, the kit comprises one or more nucleic acid or oligonucleotides that selectively hybridize with a nucleic acid encoding or associated with CD3, CD4, CD8, CD25, L-selectin, a tyrosine phosphatase, and/or a cellular or nuclear proliferation-associated marker protein. A reagent of the kit, such as an antibody, aptamer, nucleic acid, or oligonucleotide can optionally be labeled with a detectable label, and/or the kit can optionally comprise a detectable label that can be conjugated or bound to a reagent of the kit, such as an antibody, aptamer, nucleic acid, or oligonucleotide. The kit can also optionally comprise additional reagents for conjugating or binding the detectable label to a reagent of the kit. In one embodiment, a kit of the invention can optionally comprise instructions pertaining to the use of the reagents and/or methods of the invention, packaging materials, sample diluents, buffers, wash reagents, and/or containers.

Detectable labels that can be used with the present invention include, but are not limited to, enzymes, radioisotopes, chemiluminescent and bioluminescent reagents, and fluorescent moieties. Enzymes that can be used include but are not limited to lucerifase, beta-galactosidase, acetylcholinesterase, horseradish peroxidase, glucose-6-phosphate dehydrogenase, and alkaline phosphatase. If the detectable label is an enzyme, then a suitable substrate that can be acted upon by the enzyme can be used for detection and measurement of enzyme activity. In one embodiment, if the detectable label is a peroxidase, the substrate can be hydrogen peroxide ($H_2O_2$)

and 3-3'-diaminobenzidine or 4-chloro-1-naphthol and the like. Other substrates suitable for use with other enzymes are well known in the art. An example of a luminescent material includes luminol. Examples of bioluminescent materials include, but are not limited to, luciferin, green fluorescent protein (GFP), enhanced GFP (Yang et al., 1996), and aequorin. Fluorescent moieties include, but are not limited to, umbelliferone, fluorescein, fluorescein isothiocyanate, Cascade Blue, rhodamine, dichlorotriazinylamine fluorescein, dansyl chloride, Texas Red, Oregon Green, cyanines (e.g., CY2, CY3, and CY5), allophycocyanine, or phycoerythrin. Isotopes that can be used include, but are not limited to, $^{125}I$, $^{14}C$, $^{35}S$, and $^3H$.

Antibodies contemplated for use in the present invention can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. Antibodies useful in the methods of the present invention can be monoclonal or polyclonal antibodies, and can be from any source including, but not limited to, mouse, rabbit, goat, rat, or human. Antibodies of the invention can be conjugated to a detectable label, such as, for example, a fluorescent moiety. In one embodiment of the present invention, a detectable label can be directly bound to an antibody that binds to a marker of the invention. If the detectable label is to be directly bound, the label may comprise a functional group which is capable of binding to the antibody used with the invention. Alternatively, the detectable label may be indirectly bound, for example, using an avidin-biotin or streptavidin-biotin bridge wherein the avidin or biotin is labeled with a detectable label. In one embodiment, an antibody of the invention is conjugated with avidin and the detectable label is conjugated with biotin.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments, which are capable of crosslinking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

Antibody fragments can retain an ability to selectively bind with the antigen or analyte and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) $(Fab')_2$ is the fragment of an antibody that can be obtained by treating whole antibody with the enzyme pepsin without subsequent reduction. $F(ab')_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269 315 (1994).

Compounds useful in the treatment methods of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject compounds include ethanol, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject compounds based on the weight of the total composition including carrier or diluent.

As used herein, the term "myelodysplastic syndromes" or "MDS" means any hematopoietic cell disorders characterized by one or more of the following: decreased or ineffective blood cell production, anemia, cytogenetic abnormalities, cytopenias, and risk of progression to acute leukemia or cellular marrow with impaired morphology and maturation. The term "myelodysplastic syndromes" or "MDS" can include any of the following: refractory anemia (RA), refractory anemia with ringed sideroblasts (RARS), refractory anemia with excess blasts (RAEB), refractory anemia with excess blasts in transformation (RAEB-T) and chronic myelomonocytic leukemia (CMML).

Patient responsiveness to IST for a particular disorder can be based on a measurable parameter that is indicative of patient improvement after receiving a therapeutic treatment. Patient responsiveness to IST in MDS patients includes observing increases in red blood cell production; increases in granulocyte production; and increases in platelet production. In one embodiment, responsiveness to IST in MDS patients is based on hematological improvement as assessed by the International Working Group (IWG) criteria (Cheson et al., 2006; Soand et al., 2008).

MATERIALS AND METHODS

Patients and healthy controls. Seventy-six MDS patients were analyzed in total. Untreated MDS patients (n=47) were recruited from the Malignant Hematology clinic at the H. Lee Moffitt Cancer Center & Research Institute. Diagnoses were confirmed by pathology and classified in accordance with World Health Organization criteria. After obtaining written informed consent, 40 mls of peripheral blood were collected in heparinized tubes from each patient. Samples from 29 patients were obtained in collaboration with Dr. Elaine Sloand of the National Heart Lung and Blood Institute (NHLBI), Bethesda, Md. Twenty patients had been treated with ATG alone or ATG plus cyclosporine, and samples were analyzed before and after therapy. For use as controls, buffy coats from healthy blood donors were obtained from the Southwest Florida Blood Services (SFBS) in St. Petersburg, Fla. Peripheral blood mononuclear cells (PBMCs) were isolated from MDS patients and healthy donors by Ficoll-Hypaque (Amersham Pharmacia Biotech, Piscataway, N.J., USA) gradient centrifugation, as previously described, and frozen in liquid nitrogen (Epling-Burnette et al., 2001).

Detection of naïve and memory T-cell subpopulations. Cryopreserved PBMCs were thawed and incubated with antibodies to distinguish naïve and memory CD4 and CD8 T-cell subtypes were detected after surface staining with anti-CD3-PE Cy7, anti-CD45RA-FITC, anti-CD62L-APC, and either anti-CD4- or CD8-APC Cy7, which were all obtained from BD Biosciences, San Jose, Calif. USA. Naïve and memory T-cell populations were distinguished by CD45RA and CD62L expression, as described previously by flow cytometry (Maldonado et al., 2003; Rabin et al., 1995). Exclusion of DAPI was used to distinguish cell viability. Results of flow cytometry were analyzed on a LSRII Benchtop analyzer (BD Bioscience).

Flow cytometry to detect proliferation. Cell proliferation was measured by Ki-67 nuclear antigen expression. Ki-67 is expressed by cells in late G1, S, G2, and M phase of the cell cycle (Hazenberg et al., 2000a; Hellerstein et al., 1999). In earlier studies, Ki-67 staining was positively correlated with deuterated glucose labeling of dividing cells in vivo (Hellerstein et al., 1999). To determine the percentage of proliferating cells within specific lymphocyte subsets, a gate was used to define CD3+ T-cells that were CD4+ or CD8+ and stained with anti-Ki-67+ antibodies within the lymphocyte gate (R1, in FIG. 1) to determine expression in naïve and memory T-cell subsets based on CD45RA and CD62L surface markers. Anti-Ki-67-PE was used to stain the intracellular nuclear antigen after subsequent fixation and permeabilization (BD Biosciences fix and perm kit) as recommended by the manufacturer.

Statistical Analysis. The statistical methods used included linear regression, the Wilcoxon rank sum test and the Wilcoxon signed rank test (in the instances of paired data). When adjustment for multiple testing was necessary, the Holm step down method was used. A two-sided P<0.05 was considered as statistically significant. The specific statistical tests that were used in each experiment are noted in the figure and table legends.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Clinical Characteristics of MDS Patients

Characteristics of 76 untreated MDS patients (46 from Moffitt and 29 from NHLBI) are summarized in Table 1. Patient ages ranged from 19 to 82 years with a mean age of 64 years. Nearly half of the patients had refractory cytopenia with multilineage displasia (RCMD), and two thirds of all patients were low or intermediate-1 based on the IPSS. Half of the patients had abnormal karyotypes, including del[5q], trisomy 8, monosomy 7, and a complex karyotype with three or more abnormalities.

TABLE 1

Characteristics of MDS patients

| | | Total (N) | % |
|---|---|---|---|
| Age | <60 y.o. | 26 | 34.7 |
| (mean = 64 y.o.) | =60 to =71 y.o. | 24 | 32.0 |
| (n = 76)* | >71 y.o. | 25 | 33.3 |
| WHO** | RA | 20 | 35.1 |
| classification | RCMD | 25 | 43.0 |
| (n = 57) | RAEB | 12 | 21.0 |
| IPSS | Lower (low/Int-1) | 39 | 69.6 |
| (n = 56)# | Higher (Int-2/High) | 17 | 30.4 |
| Karyotype | Normal | 27 | 48.2 |
| (n = 56)& | Abnormal*** | 31 | 55.4 |
| | del 5q | 4 | |
| | Trisomy 8 | 8 | |
| | Monosomy 7 | 2 | |
| | Complex | 13 | |

*A total of 76 patients were included in this study with a mean age of 64 years. All patients met the clinical criteria for myelodysplastic syndrome based on pathological examination. The age was unavailable in 1 patient.
**World health organization (WHO) classification was assessed in 57 out of 76 patients. The classification was grouped as Refractory Anemia (RA) and refractory anemia with and refractory anemia with excess blasts 1 and 2 (RAEB).
International prognostic scoring system (IPSS) classification was available in 56 out of 76 patients. Patients were grouped as either lower (low plus intermediate-1) or intermediate-2 and high risk (higher risk). Low risk = IPSS score 0, intermediate-1 (IPSS score 0.5-1.0), intermediate-2 (IPSS score 1.5-2.0) and high risk (IPSS score >2.0).
&Karotype was performed by standard cytogenetics in 56 out of 76 patients.
***The frequency is shown for the most common abnormalities including deletion of 5q (del 5q), Trisomy 8, monosomy 7, and complex. Complex abnormalities include 3 or greater karyotypic abnormalities.

Example 2

Reduced CD4:CD8 Ratio in MDS Patients

CD4+ T-cells are normally present in the peripheral blood lymphocyte pool at 2 to 4 times greater than that of CD8+ T-cells, and diminished CD4:CD8 ratio has been previously shown to correlate with poor survival outcome in MDS (Bennett & Komrokji, 2005; Sokol et al., 1989; Kook et al., 2001; Saunthararajah et al., 2001; Wang et al., 2006; Okamoto et al., 1997). Similar to previous reports, we found that the CD4:CD8 ratio was reduced in MDS patients compared to healthy controls after adjusting for age (p-value<0.0001) (FIG. 1A).

Figure 1B:
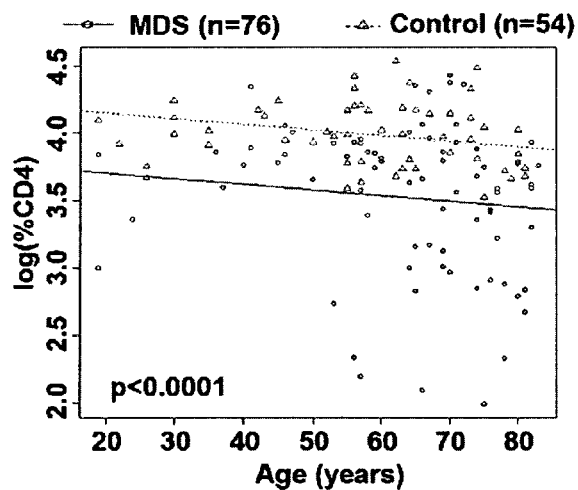
Figure 1C:
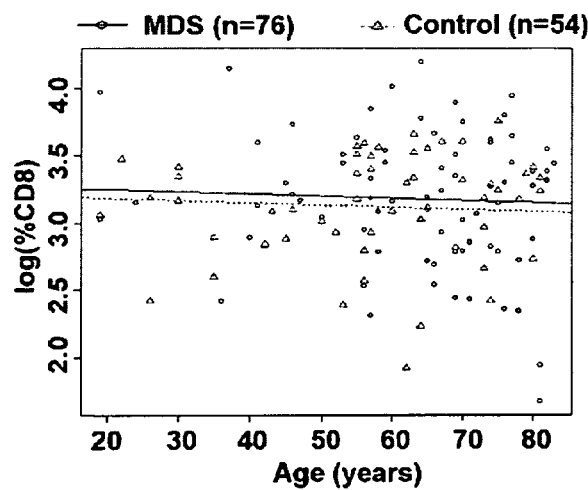

To assess whether the case-control difference in the CD4: CD8 ratio was due to differences in CD4, CD8, or both, percentages of each cell type were individually compared between cases and controls after adjusting for age. This analysis revealed that the percentage of CD4 cells was reduced in the peripheral lymphocyte pool among MDS cases as compared to controls (FIG. 1B, p-value<0.0001), while there was no difference in the percentage of CD8 cells (FIG. 1C, p-value=0.42). There was no statistically significant interaction between age and reduction in CD4:CD8 ratio in this analysis. These results suggest that changes in the CD4+ lymphocyte pool may be responsible for the diminished CD4: CD8 ratio with well-described significance in MDS (Bennett & Komrokji, 2005; Sokol et al., 1989; Kook et al., 2001; Saunthararajah et al., 2001; Wang et al., 2006; Okamoto et al., 1997).

Example 3

Figure 2:
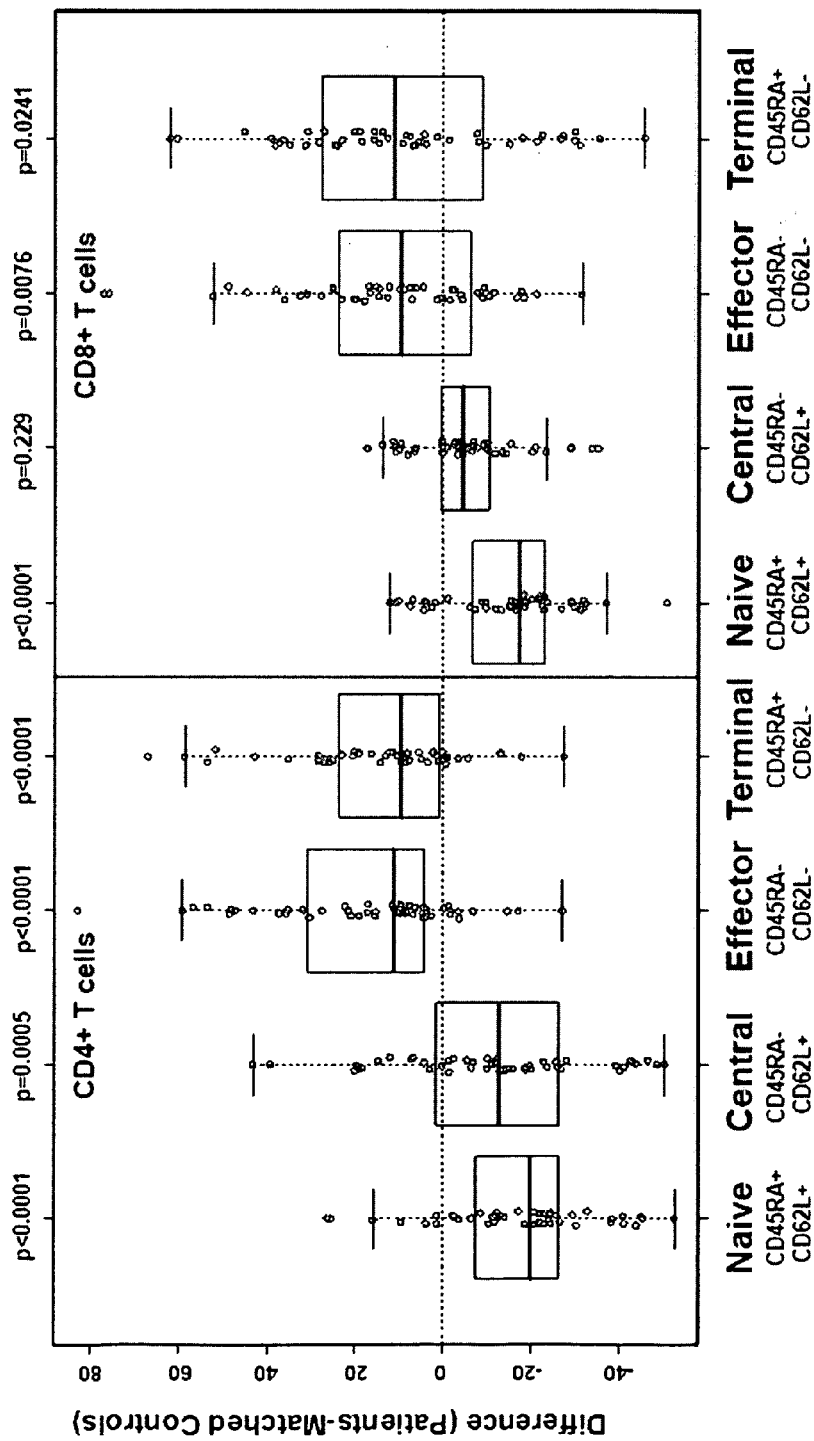
FIG. 2 shows naïve and memory phenotype analysis in MDS patients and healthy controls. Case-control differences between T-cell subpopulations were compared in 47 MDS patients and 47 healthy controls using the Wilcoxon signed rank test adjusting for multiple testing using the Holm step down method. P-values for the case-control differences are shown at the top of each panel.

T-Cell Subset Distribution is Defective in CD4+ and CD8+ T-Cells in MDS Patients Since we found that CD4+ T-cells are diminished in MDS patients, and CD8+ T-cells have been shown to display TCR repertoire restriction, we examined the phenotype of both CD4+ and CD8+ T-cell populations in the same group of MDS cases and controls. Isoforms of the tyrosine phosphatase CD45 (RB, RA, RO), along with L-selectin (CD62L), have been used to distinguish naïve from memory T-cells (Rabin et al., 1995; Sallusto et al., 1999; De Rosa et al., 2001; Champagne et al., 2001). We used multiple color flow staining to distinguish the T-cell subpopulations. An illustration of these markers is shown in supplemental FIG. 1 for a healthy control donor. We compared the proportion of circulating naïve and memory CD4+ and CD8+ T-cell subpopulations in MDS patients (n=47) and healthy control donors, individually age-matched to MDS patients within 4 years (n=47). Data in FIG. 2 show that the percentages of naïve CD4+ and CD8+ T-cells are lower in MDS. In the T-cell pool, both CD4+ and CD8+ naïve cells were under-represented in cases compared to controls (p<0.0001 for both populations). In addition to reduced naïve cells, the memory CD4+ and CD8+ subpopulations displaying a CD45RA−/CD62L− (effector memory) and CD45RA+/CD62L− (terminal effector memory) phenotype were increased in cases compared to controls.

Since the proportion of naïve and memory T-cell distributions change with age due to reduction in thymic function, the age-related differences among the MDS cases, which ranged from 19 to 82 years old (n=47), was compared to control with results shown in FIG. 3. Furthermore, T-cell homeostatic mechanisms have been reported to differ among CD4 and CD8 populations with age (Naylor et al., 2005; Czesnikiewicz-Guzik et al., 2008; Goldrath & Bevan, 1999; Schwab et al., 1997). Among these cases, positive correlations were observed between age and both % CD62L positive naïve cells and central memory CD4+ T-cells, although the former association was not statistically significant (naïve: slope=0.186, p=0.14; central memory: slope=0.685, p=0.001). Furthermore, the proportions of CD62L− CD4+ T-cell populations, including effector memory and terminal effector memory T-cells, were greater in younger MDS patients (slope=−0.433, p=0.128 and slope=−0.364, p=0.128, respectively). Similar patterns with age were observed for naïve, central memory, effector memory and terminal effector memory CD8+ T-cells, although the associations were weaker than those observed for CD4+ T-cells, and only the reduction in central memory cells in younger patients was statistically significant (FIG. 3B, slope=−0.249, p=0.022). These age-related changes in T-cell phenotype were distinctly different from those observed in CD4+ or CD8+ T-cells from controls, as shown in FIG. 3, that ranged in age from 19 to 81 years old (n=54). Although there was a slight tendency for CD4+ naïve cells to decrease with age, this trend was not statistically significant (slope=−0.11, p=1.0), and central, effector, and terminal effector memory CD4+ T-cell subpopulations did not change with age within the CD4+ subset (FIG. 3C). In these healthy control donors, a dramatic age-related change in T-cell homeostasis occurred within the CD8+ T-cell compartment. The percentage of naïve CD8+ T-cells decreased 0.61% with each year of age (p=<0.0001); whereas, conversion of the peripheral pool to terminal effector memory cells was positively associated with age (0.567% increase with each year of age, p=0.001), as shown in FIG. 3D (left panel). In summary, results show that there is a particular skewing of CD4+ and CD8+ T-cells toward a CD62L− phenotype with reduction in naïve cells in younger MDS patients.

Example 4

Figures 1, 2, 4A, 4B:
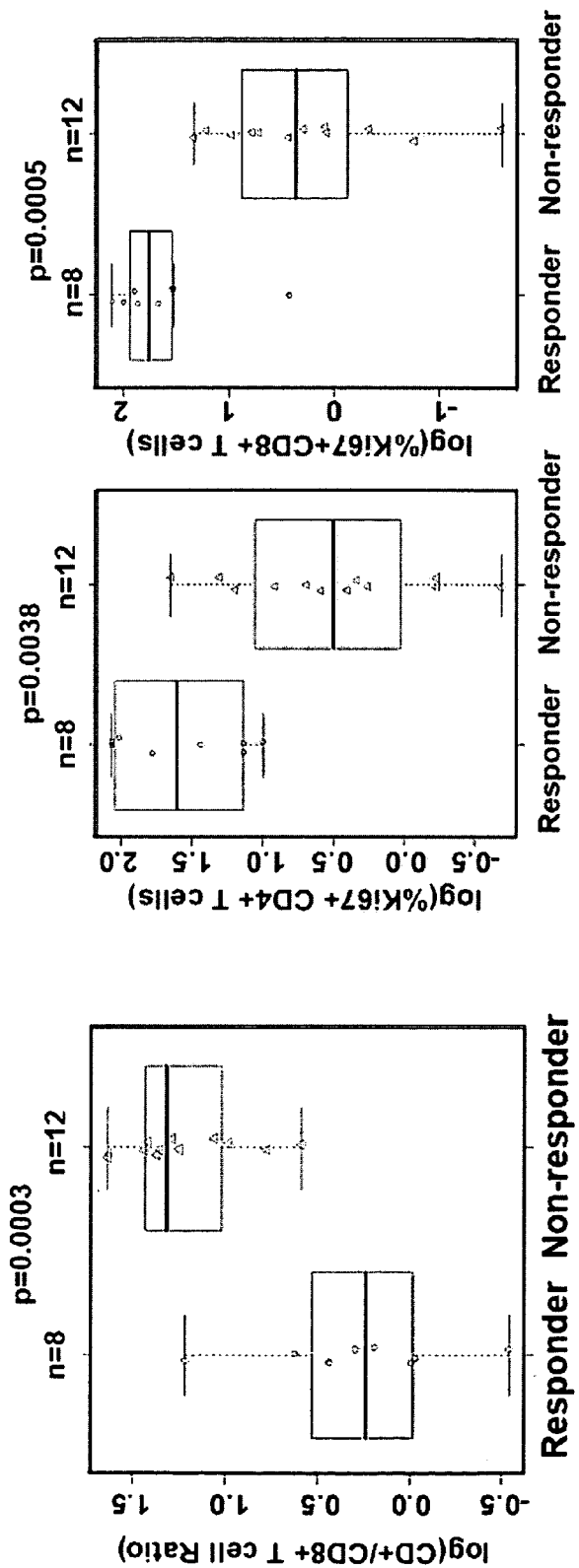

Aberrant Homeostatic T-Cell Regulation Prior to Treatment in Patients Responsive to IST Diminished naïve T-cells may result from accelerated turnover characterized by increased cell death or increased conversion of naïve cells into memory cells similar to abnormalities observed in association with other autoimmune syndromes (Krupica et al., 2006; Marleau & Sarvetnick, 2005; Goronzy & Weyand, 2005; Fulop et al., 2003). Since younger age in MDS represents an important characteristic related to IST response, the CD4+ and CD8+ naïve and memory cell populations and the CD4:CD8 ratio were compared among eight IST responders and fifteen non-responders (ages ranged from 19 to 72 years old with a mean age of 46 and 62 years among responders and non-responders, respectively) to gain a better understanding of how altered T-cell homeostasis impacts bone marrow suppression among younger cases. To understand the relationship between T-cell turnover and IST response, we also determined the expression of Ki-67, a nuclear proliferation-associated antigen, as an indicator of proliferation in both the CD4+ and CD8+ T-cells. Patients were treated with either equine anti-thymocyte globulin (ATG) or ATG plus cyclosporine A (CyA), and hematologic response was assessed using the International Working Group (IWG) criteria with clinical results reported elsewhere (Cheson et al., 2006; Sloand et al., 2008). First, immune parameters were compared before treatment between patients that demonstrated hematologic response (complete response and partial response) and patients demonstrating no clinical hematologic improvement to this therapy. We found that the CD4:CD8 ratio before treatment was statistically significantly lower in the IST responders compared to non-responders (FIG. 4A) (p=0.0003). Interestingly, we found that the pre-treatment % of Ki-67 positive cells in both the CD4+ and CD8+ subpopulations was significantly greater in MDS patients demonstrating a response to IST compared to patients who did not respond (p=0.0038 and p=0.0005, respectively, FIGS. 4B-1 and 4B-2). In FIGS. 4C-1 and 4C-2, we show inverse correlations between the percentage of Ki-67+/CD4+ and Ki-67+/CD8+ T-cells and the CD4: CD8 ratio, which was statistically significant for the CD4+ population (p=0.0123 for CD4+ and p=0.0619 for CD8+ cells while adjusting for age). These results suggest that cells within both of these compartments are actively cycling when the ratio is diminished in MDS patients.

Example 5

Figure 5A:
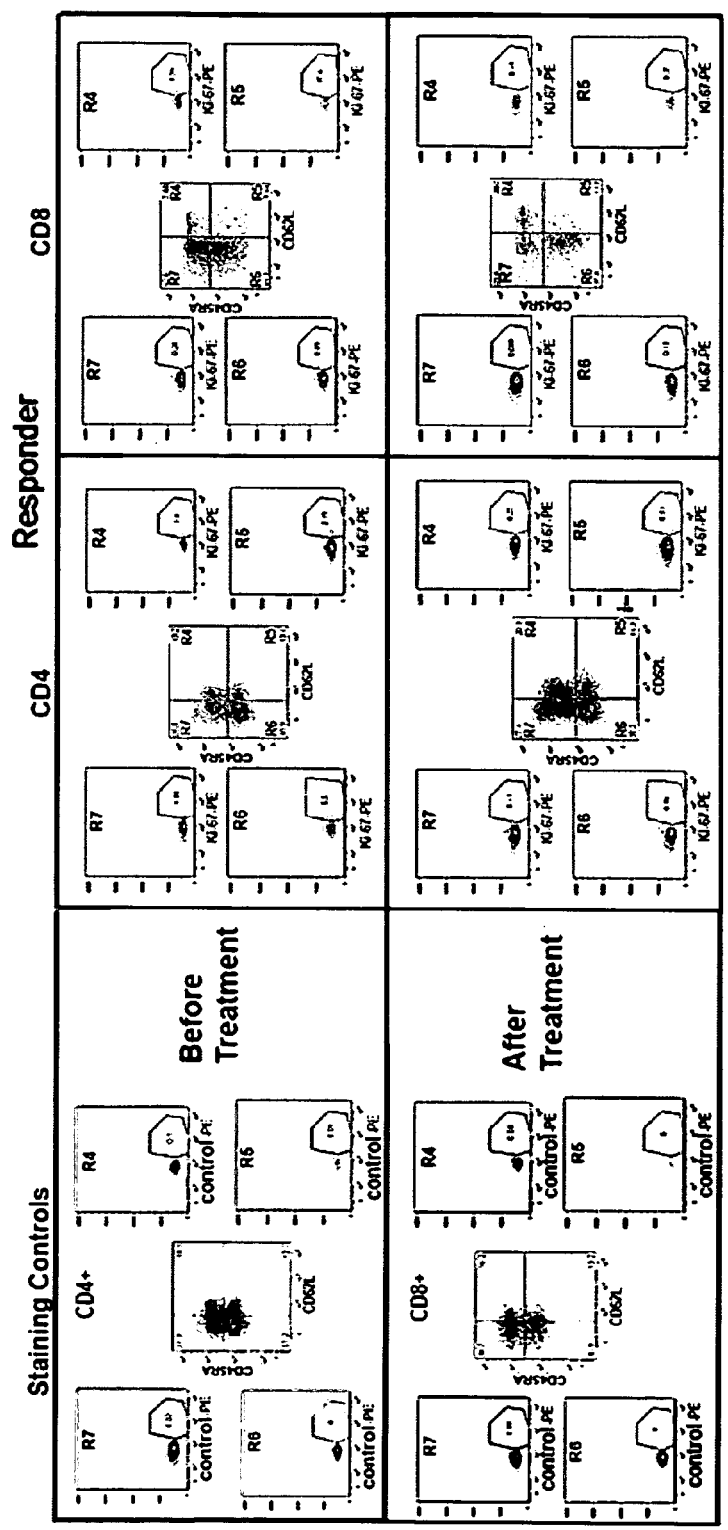
FIGS. 5A-5C show the change in T-cell homeostasis after therapy in IST responsive and non-responsive patients. After labeling T-cell surface markers, the first gate was given to lymphocytes (as shown in FIG. 1A). T-cells were identified by anti-CD3-antibody staining (as shown in FIG. 1B), gates were then set to distinguish CD8– (CD4+) and CD8+ T-cells populations (as shown in FIG. 1C).
Figure 5B:
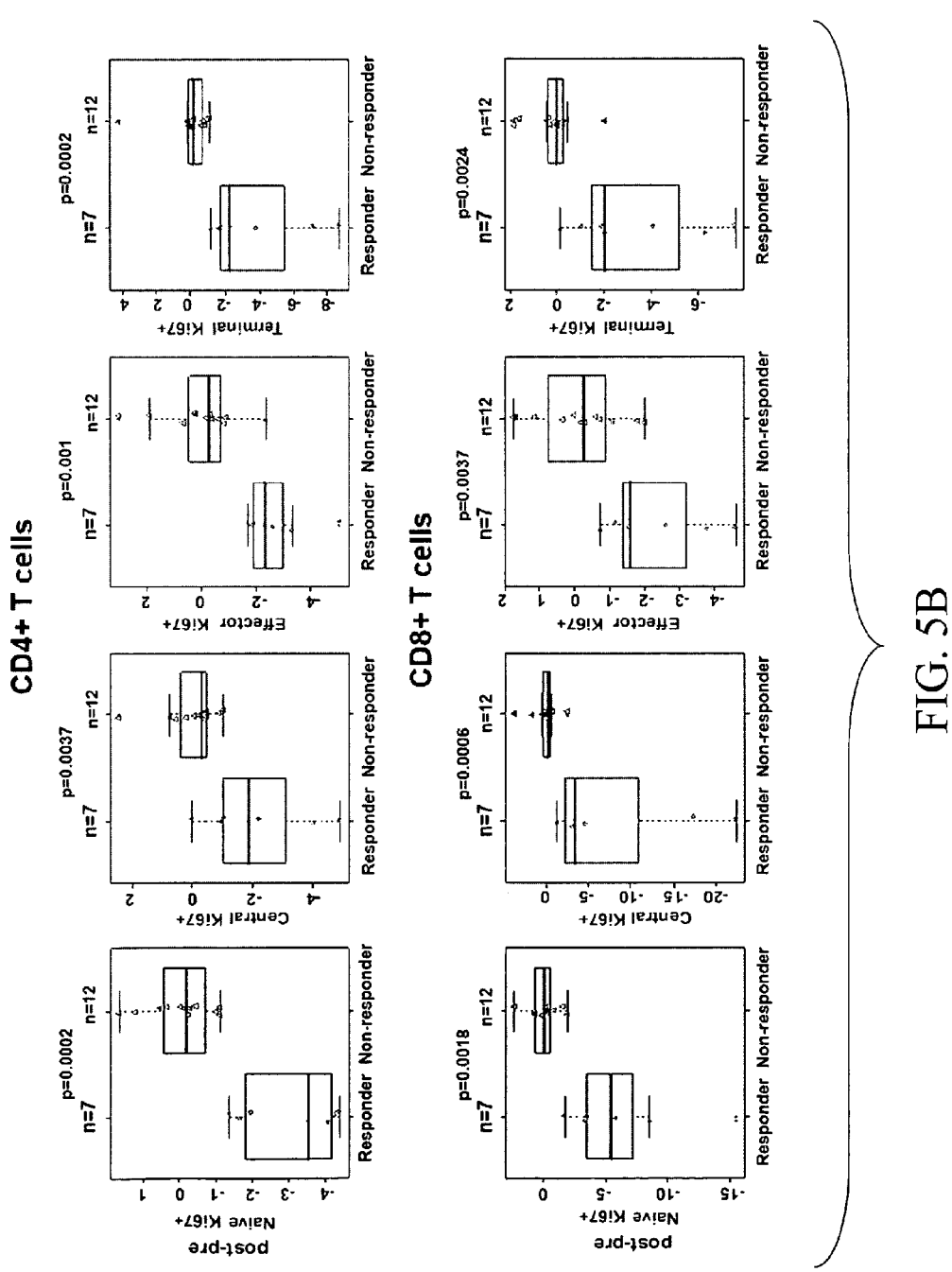
Figure 5C:
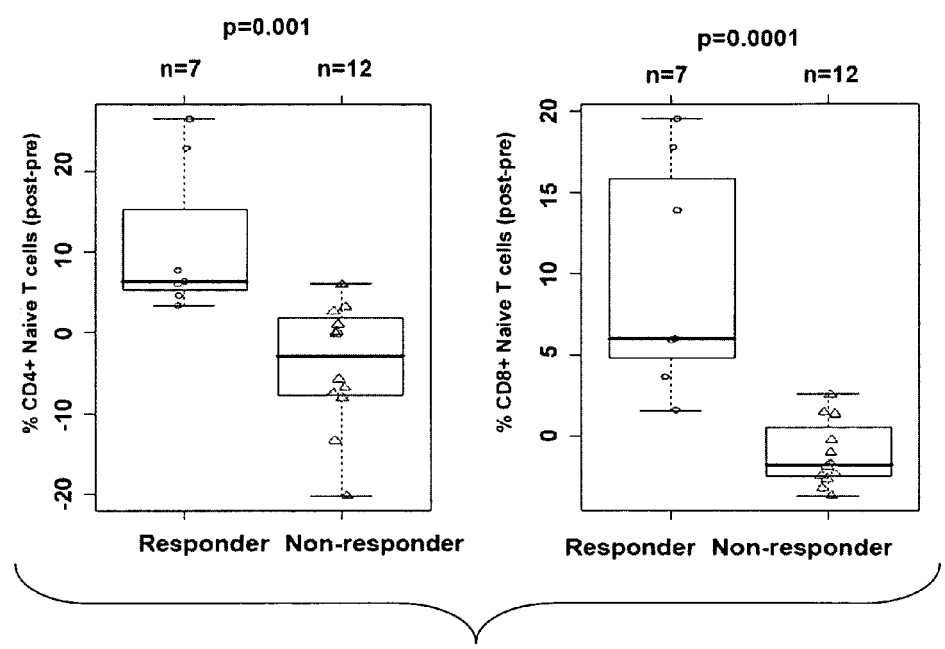
Figures 6A, 6B, 6C, 6D:
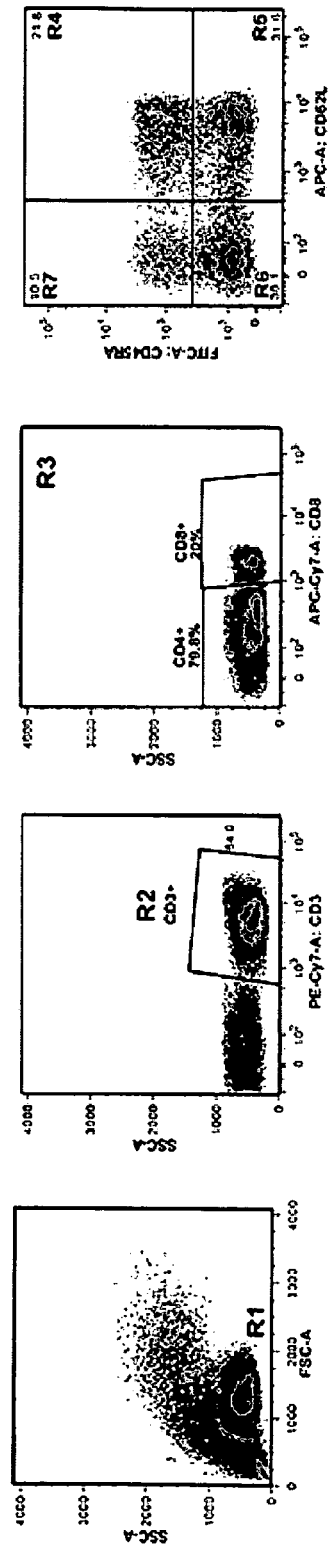
FIGS. 6A-6E show phenotype using CD45RA/CD62L display. In some experiments, anti-CCR7-PE was also included. Anti-perforin-PE and anti-IFNγ-PE antibodies were used to stain permeabilized cells (BD Biosciences fix and perm kit). Induction of IFNγ release was determined after activation with plate-bound anti-CD3 antibody and anti-CD28 (BD Pharmingen, San Jose, Calif. USA) cross-linking. Stimulation with anti-CD28 along (5 ng/ml) was used as a negative control. Brefeldin A (10 μg/ml, Sigma, Calif. USA) was added during the last 4 hrs of the stimulation period to prevent extracellular secretion. CD45RA/CD62L populations (R4-R7) were defined in both CD4+ and CD8+ T-cell subsets as follows: naive CD62L+/CD45RA+, central memory CD62L+/CD45RA–, effector memory CD62L–/CD45RA–, and terminal effector memory CD62L–/CD45RA+ as shown in FIGS. 6A-6D. The percentage of cells that expressed the chemokine receptor CCR7, perforin, and anti-CD3-induced IFNγ in each subpopulation is shown in FIG. 6E. Similar to previous reports, IFNγ production and perforin expression were almost exclusively restricted to CD62L negative memory subsets (R6 and R7), whereas CCR7 expression was strongly associated with a naive phenotype (CD45RA+/CD62L+, R4) (FIG. 6E) (Sallusto et al., 1999).
Figure 6E:
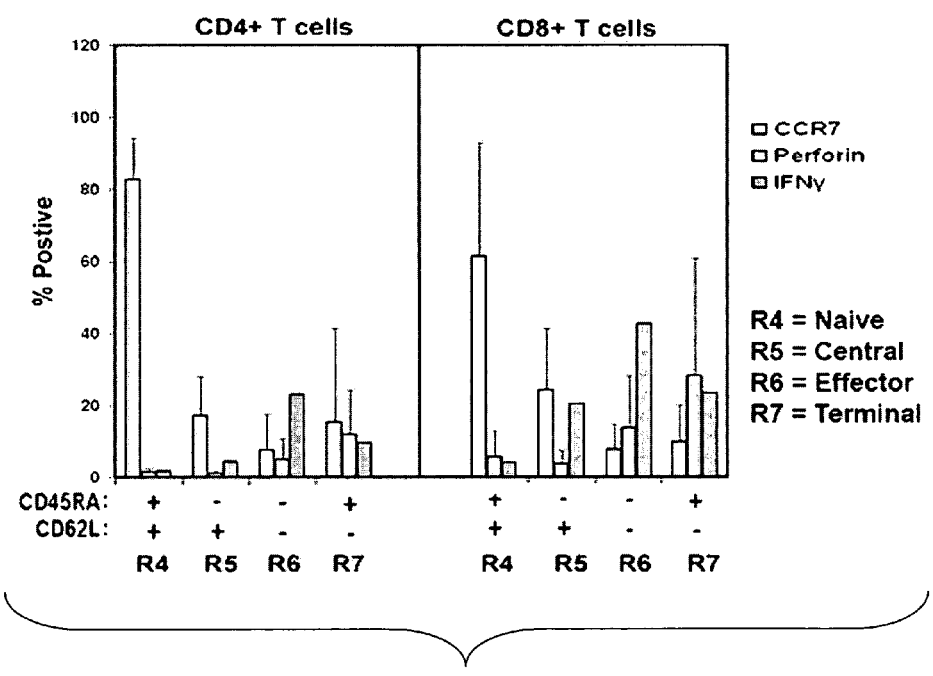

Reconstitution of T-Cell Homeostasis is Associated with Recovery of Bone Marrow Hematopoiesis after Therapy Next, we compared the changes in key immune parameters before and after IST in association with clinical hematologic response. The proliferative index is dramatically reduced after treatment specifically in the IST responsive patients as compared to the non-responsive patients in both the CD4+ and CD8+ T-cells as demonstrated by Ki-67 expression. To determine whether the changes in proliferation affected all of the CD4+ and CD8+ subpopulations, individual analyses were performed on naïve and memory cells defined by % Ki67 in association with CD45RA and CD62L staining using the gating strategy shown in FIG. 5A. After treatment, a reduction in Ki-67 expression was observed in naïve and all memory subpopulations after IST in patients with a hematological response compared to changes in the non-responders (FIG. 5B, $p<0.05$ for all tests). These results strongly suggest that proliferation may be coupled to accelerated T-cell depletion and altered T-cell homeostasis that eventually leads to a reduction in naïve cells. Consistent with this idea, patients demonstrating a hematological response to IST displayed an increase in naïve CD4+ and CD8+ T-cells after treatment compared to non-responders (FIG. 5C) ($p=0.001$ and $p=0.0001$, respectively). In summary, results show that proliferation in T-cells is higher and the CD4:CD8 ratio is lower before treatment in younger IST responsive patients. Furthermore, results also demonstrate that hematological response is associated with reconstitution of T-cell homeostasis and reduction in homeostatic proliferation.

Example 6

Since little is known about age as a modifier of immunity in MDS, the current study was conducted to determine whether T-cell homeostasis and function is normal and age-appropriate in MDS patients. Unlike most previously reported findings in CD8+ T-cells, we found that contraction of naïve and central memory cells and accumulation of effector and terminal effector memory cells were also pronounced within the CD4+ T-cell compartment in younger MDS patients and that reduction in the CD4:CD8 ratio was driven by an age-independent decrease in CD4+ T-cells (Molldrem et al., 1998; Saunthararajah et al., 2001; Molldrem et al., 2002; Sloand et al., 2005). To discern how these age-related abnormalities defined in the case-control study may impact bone marrow suppression, we studied T-cell immunity in 20 MDS patients before and after treatment with ATG with or without CyA. Results presented here strongly suggest that reduced CD4+ T-cells not only drive the aberrant CD4:CD8 ratio in a diverse group of MDS patients but is also robustly associated with IST responsiveness in younger patients. In addition to reduced CD4+ T-cells, altered naïve and memory subset distribution was found in CD4+ T-cell and CD8+ cells.

In younger MDS patients, fragility of the CD4+ naïve T-cell compartment is strikingly different than changes associated with a normal aging process where CD4+ naïve cells remain constant, as shown in FIG. 3. In healthy controls, our results are consistent with previous studies showing that regulation of CD4+ and CD8+ homeostasis occurs through distinct mechanisms during the aging process. CD4+ T-cells from patients are clearly more vulnerable to depletion compared to controls (Naylor et al., 2005). There are several examples, including rheumatoid arthritis, infection with human immunodeficiency virus (HIV)-1, and individuals with repeated pathogen exposure, where peripheral CD4+ naïve T-cells are diminished and the CD4:CD8 ratio shifted in association with chronic activation (Hazenberg et al., 2000a; Hazenberg et al., 2000b; Goronzy & Weyand, 2001). Therefore, these results suggest that CD4+ T-cells in addition to CD8+ T-cells have been activated in vivo.

Reduction in naïve cells in MDS may be mediated by either increased apoptotic sensitivity or increased rate of phenotype conversion to memory cells (Hazenberg et al., 2000b; Weyand & Goronzy, 1999). A mechanism of increased sensitivity to apoptosis is consistent with previous findings that hypocellularity, in some studies, is associated with clinical responsiveness to IST (Lim et al., 2007; Sun et al., 2008). Greater susceptibility to Fas-mediated apoptosis and higher levels of TNFα have also been consistently linked to bone marrow failure in not only MDS but also in LGL leukemia (Sloand et al., 2002; Gersuk et al., 1998; Powers et al., 2007; Galili et al., 2007; Reza et al., 1999; Reza et al., 1998). A higher proliferative index, especially affecting naïve cells, in younger IST-responsive MDS cases indicates that T-cells in these patients have been exposed to conditions which promote non-antigen-specific proliferation (i.e., homeostatic proliferation) driven by the IL-2Rβ$γ_c$ family of cytokines IL-7, IL-15, and/or IL-21 that are associated with risk for autoimmunity in many situations (Clarke & Rudensky, 2000; Lim & Kim, 2007; Chiu et al., 2006).

An increase in T-cell homeostatic proliferation in response to the IL-2Rβ$γ_c$ leads to the indiscriminate expansion of both non-thymic-depleted self-reactive T-cells and antigen-specific T-cells. An increase in homeostatic proliferation alone, however, generally fails to induce autoimmunity. It is the combination of homeostatic proliferation and defects in one or more additional factor(s) circumventing mechanisms of peripheral tolerance that leads ultimately to autoimmunity in this setting (Krupica et al., 2006). It is possible that loss of the CD4+ T-cells in MDS may represent depletion or functional inactivation of a specific subset of CD4+ T-cells, namely regulatory T-cells (Tregs), which are important for peripheral tolerance and prevention of an autoimmune process (Stockinger et al., 2004; Setoguchi et al., 2005; Neujahr et al., 2006; Calzascia et al., 2008). Tregs express high levels of CD25 (IL-2Ra) with low (dim) expression of IL-7Rα (CD127) and suppress CD4+ and CD8+ responses to not only TCR stimulation but also homeostatic proliferation (Krupica et al., 2006; Dunham et al., 2008; Vrabelova et al., 2008; Alves et al., 2007). Tregs can develop in the thymus (natural, nTregs) or they can be expanded in the periphery (inducible Tregs, iTregs) (Valencic et al., 2007). Tregs are characterized by the expression of the FOXP3 transcription factor with greater expression of the negative co-stimulatory molecule cytotoxic T lymphocyte-associated antigen (CTLA-4) (Catalfamo et al., 2008). The number of Tregs in the peripheral blood of MDS patients has been shown to positively correlate with risk for disease progression. Further investigation is needed to determine whether the number and/or function of Tregs is lower in IST responsive patients compared to healthy controls with age adjustment. The latter is important since Treg number and/or function may vary with age (Kordasti et al., 2007; Czesnikiewicz-Guzik et al., 2008). Furthermore, elevated levels of IL-21 have recently been shown to suppress Treg function without affecting cell numbers. In addition to Treg reduction, excessive IL-21 (King et al., 2004) or an inflammatory microenvironment independently act as catalyzing factors for homeostatic proliferation-associated autoimmunity (Krupica et al., 2006).

Regardless of the cellular mechanisms that govern the proliferation and turnover in the T-cell compartment, the association between the T-cell abnormalities reported in this study and response to IST provides a strong rationale implicating aberrant T-cell homeostasis as a critical determinant of autoimmunity in MDS that may have positive predictive power for response to IST. In summary, our findings are consistent with a model that IST blocks the proliferative signal that is associated with depletion of CD4+ T-cells and expansion of autoreactive CD8+ T-cells, and restores T-cell-homeostasis of the CD4+ and CD8+ T-cell compartment. The presence of altered T-cell homeostasis may represent a marker that is predictive for IST responsiveness.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,582,789
U.S. Pat. No. 4,617,261
U.S. Pat. No. 4,683,195
Alves, N. L. et al. (2007) A new subset of human naive CD8+ T cells defined by low expression of IL-7R alpha. J Immunol 179, 221-8.
Ausubel et al., eds (1994) Current Protocols in Molecular Biology, Vol. 1, John Wiley and Sons, Inc., New York.
Bennett, J. M. & Komrokji, R. S. (2005) The myelodysplastic syndromes: diagnosis, molecular biology and risk assessment. Hematology 10 Suppl 1, 258-69.
Berezovski, M. V., Lechmann, M., Musheev, M. U., Mak, T. W., Krylov, S. N. (2008) Aptamer-facilitated biomarker discovery (AptaBiD). J Am Chem Soc. 130 (28): 9137-43.
Biesma, D. H., van den Tweel, J. G. & Verdonck, L. F. (1997) Immunosuppressive therapy for hypoplastic myelodysplastic syndrome. Cancer 79, 1548-51.
Calzascia, T. et al. (2008) CD4 T cells, lymphopenia, and IL-7 in a multistep pathway to autoimmunity. Proc Natl Acad Sci USA 105, 2999-3004.
Catalfamo, M., Tai, X., Karpova, T., McNally, J. & Henkart, P. A. (2008) TcR-induced regulated secretion leads to surface expression of CTLA-4 in CD4(+)CD25(+) T cells. Immunology 125(1), 70-79.
Champagne, P. et al. (2001) Skewed maturation of memory HIV-specific CD8 T lymphocytes. Nature 410, 106-11.
Cheson, B. D. et al. (2006) Clinical application and proposal for modification of the International Working Group (IWG) response criteria in myelodysplasia. Blood 108, 419-25.
Chiu, W. K., Fann, M. & Weng, N. P. (2006) Generation and growth of CD28nullCD8+ memory T cells mediated by IL-15 and its induced cytokines. J Immunol 177, 7802-10.
Clarke, S. R. & Rudensky, A. Y. (2000) Survival and homeostatic proliferation of naive peripheral CD4+ T cells in the absence of self peptide:MHC complexes. J Immunol 165, 2458-64.
Colmegna, I. et al. (2008) Defective proliferative capacity and accelerated telomeric loss of hematopoietic progenitor cells in rheumatoid arthritis. Arthritis Rheum 58, 990-1000.
Czesnikiewicz-Guzik, M. et al. (2008) T cell subset-specific susceptibility to aging. Clin Immunol 127, 107-18.
De Rosa, S. C., Herzenberg, L. A., Herzenberg, L. A. & Roederer, M. (2001) 11-color, 13-parameter flow cytometry: identification of human naive T cells by phenotype, function, and T-cell receptor diversity. Nat Med 7, 245-8.
Dunham, R. M. et al. (2008) CD127 and CD25 Expression Defines CD4+ T Cell Subsets That Are Differentially Depleted during HIV Infection. J Immunol 180, 5582-92.
Ellington, A. D., and Szostak, J. W. (1990) In vitro selection of RNA molecules that bind specific ligands. Nature 346 (6287): 818-22.
Epling-Burnette, P. K. et al. (2001) Inhibition of STAT3 signaling leads to apoptosis of leukemic large granular lymphocytes and decreased Mcl-1 expression. J Clin Invest 107, 351-62.
Fulop, T., Jr., Larbi, A., Dupuis, G. & Pawelec, G. (2003) Ageing, autoimmunity and arthritis: Perturbations of TCR signal transduction pathways with ageing—a biochemical paradigm for the ageing immune system. Arthritis Res Ther 5, 290-302.
Galili, N., Cerny, J. & Raza, A. (2007) Current treatment options: impact of cytogenetics on the course of myelodysplasia. Curr Treat Options Oncol 8, 117-28.
Gersuk, G. M. et al. (1998) A role for tumour necrosis factor-alpha, Fas and Fas-Ligand in marrow failure associated with myelodysplastic syndrome. Br J Haematol 103, 176-88.
Goldrath, A. W. & Bevan, M. J. (1999) Selecting and maintaining a diverse T-cell repertoire. Nature 402, 255-62.
Goronzy, J. J. & Weyand, C. M. (2005) Rheumatoid arthritis. Immunol Rev 204, 55-73.
Goronzy, J. J. & Weyand, C. M. (2001) Thymic function and peripheral T-cell homeostasis in rheumatoid arthritis. Trends Immunol 22, 251-5.
Greenberg, P. et al. (1997) International scoring system for evaluating prognosis in myelodysplastic syndromes. Blood 89, 2079-88.
Hazenberg, M. D. et al. (2000a) T-cell division in human immunodeficiency virus (HIV)-1 infection is mainly due to immune activation: a longitudinal analysis in patients before and during highly active antiretroviral therapy (HAART). Blood 95, 249-55.
Hazenberg, M. D. et al. (2000b) Increased cell division but not thymic dysfunction rapidly affects the T-cell receptor excision circle content of the naive T cell population in HIV-1 infection. Nat Med 6, 1036-42.
Hellerstein, M. et al. (1999) Directly measured kinetics of circulating T lymphocytes in normal and HIV-1-infected humans. Nat Med 5, 83-9.
Hoppe-Seyler, F. and Butz, K. (2000) Peptide aptamers: powerful new tools for molecular medicine. J Mol Med. 78 (8): 426-30.
Jaroszeski, M. J. and Heller, R. (Editors) (1998) Flow Cytometry Protocols. Methods in Molecular Biology, No 91, Humana Press.
King, C., Ilic, A., Koelsch, K. & Sarvetnick, N. (2004) Homeostatic expansion of T cells during immune insufficiency generates autoimmunity. Cell 117, 265-77.

Klussmann, S. (ed.) (2006) Aptamer Handbook: Functional Oligonucleotides and Their Applications.

Kochenderfer, J. N., Kobayashi, S., Wieder, E. D., Su, C. & Molldrem, J. J. (2002) Loss of T-lymphocyte clonal dominance in patients with myelodysplastic syndrome responsive to immunosuppression. Blood 100, 3639-45.

Kook, H. et al. (2001) Increased cytotoxic T cells with effector phenotype in aplastic anemia and myelodysplasia. Exp Hematol 29, 1270-7.

Kordasti, S. Y. et al. (2007) CD4+ CD25high Foxp3+ regulatory T cells in myelodysplastic syndrome (MDS). Blood 110, 847-50.

Krupica, T., Jr., Fry, T. J. & Mackall, C. L. (2006) Autoimmunity during lymphopenia: a two-hit model. Clin Immunol 120, 121-8.

Lim, Z. Y. et al. (2007) Low IPSS score and bone marrow hypocellularity in MDS patients predict hematological responses to antithymocyte globulin. Leukemia 21, 1436-41.

Lim, H. W. & Kim, C. H. (2007) Loss of IL-7 receptor alpha on CD4+ T cells defines terminally differentiated B cell-helping effector T cells in a B cell-rich lymphoid tissue. J Immunol 179, 7448-56.

List, A. F., Vardiman, J., Issa, J. P. & DeWitte, T. M. (2004) Myelodysplastic syndromes. Hematology (Am Soc Hematol Educ Program), 297-317.

Loughran, P., Jr. (1998) Anemia in Lymphoproliferative Disorders. Cancer Control 5, 51-53.

Maldonado, A. et al. (2003) Decreased effector memory CD45RA+ CD62L− CD8+ T cells and increased central memory CD45RA− CD62L+CD8+ T cells in peripheral blood of rheumatoid arthritis patients. Arthritis Res Ther 5, R91-6.

Marleau, A. M. & Sarvetnick, N. (2005) T cell homeostasis in tolerance and immunity. J Leukoc Biol 78, 575-84.

Molldrem, J. J. et al. (1998) Haematological response of patients with myelodysplastic syndrome to antithymocyte globulin is associated with a loss of lymphocyte-mediated inhibition of CFU-GM and alterations in T-cell receptor Vbeta profiles. Br J Haematol 102, 1314-22.

Molldrem, J. J. et al. (1997) Antithymocyte globulin for patients with myelodysplastic syndrome. Br J Haematol 99, 699-705.

Molldrem, J. J. et al. (2002) Antithymocyte globulin for treatment of the bone marrow failure associated with myelodysplastic syndromes. Ann Intern Med 137, 156-63.

Naylor, K. et al. (2005) The influence of age on T cell generation and TCR diversity. J Immunol 174, 7446-52.

Neujahr, D. C. et al. (2006) Accelerated memory cell homeostasis during T cell depletion and approaches to overcome it. J Immunol 176, 4632-9.

Okamoto, T. et al. (1997) Correlation between immunological abnormalities and prognosis in myelodysplastic syndrome patients. Int J Hematol 66, 345-51.

Ormerod, M. G. (2008) Flow Cytometry—A Basic Introduction.

Powers, M. P. et al. (2007) Polymorphisms in TGFbeta and TNFalpha are associated with the myelodysplastic syndrome phenotype. Arch Pathol Lab Med 131, 1789-93.

Rabin, R. L. et al. (1995) Altered representation of naive and memory CD8 T cell subsets in HIV-infected children. J Clin Invest 95, 2054-60.

Radbruch, A. (Editor), (2000) Flow Cytometry and Cell Sorting (Springer Lab Manual), Springer Verlag.

Recktenwald, D. and Radbruch, A. (Editors) (1997) Cell Separation Methods and Applications, Marcel Dekker.

Reza, S. et al. (1999) Biologic characteristics of 164 patients with myelodysplastic syndromes. Leuk Lymphoma 33, 281-7.

Reza, S., Shetty, V., Dar, S., Qawi, H. & Raza, A. (1998) Tumor necrosis factor-alpha levels decrease with anticytokine therapy in patients with myelodysplastic syndromes. J Interferon Cytokine Res 18, 871-7.

Saiki et al. (1985) *Science,* 230:1350.

Sallusto, F., Lenig, D., Forster, R., Lipp, M. & Lanzavecchia, A. (1999) Two subsets of memory T lymphocytes with distinct homing potentials and effector functions. Nature 401, 708-12.

Saunthararajah, Y. et al. (2001) Coincident myelodysplastic syndrome and T-cell large granular lymphocytic disease: clinical and pathophysiological features. Br J Haematol 112, 195-200.

Saunthararajah, Y. et al. (2002) HLA-DR15 (DR2) is over-represented in myelodysplastic syndrome and aplastic anemia and predicts a response to immunosuppression in myelodysplastic syndrome. Blood 100:1570-1574.

Saunthararajah, Y. et al. (2003) A simple method to predict response to immunosuppressive therapy in patients with myelodysplastic syndrome. Blood 102:3025-3027.

Scharf et al., (1986) *Science,* 233:1076.

Schwab, R. et al. (1997) Expanded CD4+ and CD8+ T cell clones in elderly humans. J Immunol 158, 4493-9.

Setoguchi, R., Hori, S., Takahashi, T. & Sakaguchi, S. (2005) Homeostatic maintenance of natural Foxp3(+) CD25(+) CD4(+) regulatory T cells by interleukin (IL)-2 and induction of autoimmune disease by IL-2 neutralization. J Exp Med 201, 723-35.

Shapiro, H. M. (2003) Practical Flow Cytometry, 4th Edition, Wiley Liss, New York.

Sloand, E. M., Wu, C. O., Greenberg, P., Young, N. & Barrett, J. (2008) Factors Affecting Response and Survival in Patients With Myelodysplasia Treated With Immunosuppressive Therapy. J Clin Oncol.

Sloand, E. M. et al. (2005) Preferential suppression of trisomy 8 compared with normal hematopoietic cell growth by autologous lymphocytes in patients with trisomy 8 myelodysplastic syndrome. Blood 106, 841-51.

Sloand, E. M. et al. (2002) Fas-mediated apoptosis is important in regulating cell replication and death in trisomy 8 hematopoietic cells but not in cells with other cytogenetic abnormalities. Blood 100, 4427-32.

Sokol, R. J., Hewitt, S. & Booker, D. J. (1989) Erythrocyte autoantibodies, autoimmune haemolysis, and myelodysplastic syndromes. J Clin Pathol 42, 1088-91.

Starkebaum, G., Loughran, T. P., Jr., Gaur, L. K., Davis, P. & Nepom, B. S. (1997) Immunogenetic similarities between patients with Felty's syndrome and those with clonal expansions of large granular lymphocytes in rheumatoid arthritis. Arthritis Rheum 40, 624-6.

Steensma, D. P. & Tefferi, A. (2003) The myelodysplastic syndrome(s): a perspective and review highlighting current controversies. Leuk Res 27, 95-120.

Stockinger, B., Kassiotis, G. & Bourgeois, C. (2004) Homeostasis and T cell regulation. Curr Opin Immunol 16, 775-9.

Sun, M., Zhang, J., Liu, S., Liu, Y. & Zheng, D. (2008) Sp1 is involved in 8-chloro-adenosine-upregulated death receptor 5 expression in human hepatoma cells. Oncol Rep 19, 177-85.

Valencic, E., Piscianz, E., Tommasini, A. & Granzotto, M. (2007) T cells stimulated in vitro have a suppressive function but do not contain only regulatory T cells. Clin Exp Immunol 150, 561-6.

Vrabelova, Z. et al. (2008) CD 127– and FoxP3+ expression on CD25+CD4+ T regulatory cells upon specific diabetogeneic stimulation in high-risk relatives of type 1 diabetes mellitus patients. Scand J Immunol 67, 404-10.

Wang, H. Q. et al. (2006) Burden of abnormal hematopoietic clone in patients with myelodysplastic syndromes. Chin Med Sci J 21, 99-103.

Weyand, C. M. & Goronzy, J. J. (1999) T-cell responses in rheumatoid arthritis: systemic abnormalities-local disease. Curr Opin Rheumatol 11, 210-7.

Young, N. S. (2002) Immunosuppressive treatment of acquired aplastic anemia and immune-mediated bone marrow failure syndromes. Int J Hematol 75, 129-40.

I claim:

1. A method for treating myelodysplastic syndrome (MDS) in a patient, said method comprising:
   (a) measuring the level and/or proliferation of $CD4^+$ T cells and/or $CD8^+$ T cells in a biological sample obtained from the patient, wherein said measuring comprises quantitating a marker protein of the $CD4^+$ T cells and/or $CD8^+$ T cells by contacting the biological sample with an antibody, antibody fragment, or other moiety that binds specifically to the marker protein, wherein the biological sample has:
   a reduced or lower level of $CD4^+$ T cells relative to a value that is associated with a lack of response to immunsuppressive therapy (IST), or
   a reduced or lower ratio of $CD4^+$ $CD8^+$ T cells relative to a value that is associated with a lack of response to IST, or
   an increased or higher level of proliferation of $CD4^+$ and/or $CD8^+$ T cells relative to a value that is associated with a lack of response to IST:
   (b) selecting the patient for treatment with an IST; and
   (c) administering the IST to the selected patient.

2. The method according to claim 1, wherein the level and/or proliferation of $CD4^+$ T cells is measured.

3. The method according to claim 1, wherein the level and/or proliferation of $CD8^+$ T cells is measured.

4. The method according to claim 1, wherein the level and/or proliferation of $CD4^+$ T cells and $CD8^+$ T cells is measured.

5. The method according to claim 4, wherein proliferation is measured by detecting expression of a cellular or nuclear proliferation-associated antigen on a $CD4^+$ and/or $CD8^-$ T cell.

6. The method according to claim 4, wherein proliferation is measured by detecting the marker Ki-67.

7. The method according to claim 1, wherein the level of $CD4^+$ and/or $CD8^+$ effector memory T cells and/or terminal effector memory T cells is measured, and wherein the biological sample has increased percentage of $CD4^+$ and/or $CD8^+$ effector memory T cells and/or terminal effector memory T cells.

8. The method according to claim 1, wherein the level of $CD4^+$ effector memory T cells is measured, and wherein the biological sample has an increased percentage of $CD4^+$ effector memory T cells.

9. The method according to claim 7, wherein the level of $CD4^+$ and/or $CD8^+$ effector memory T cells and/or terminal effector memory T cells is measured by detecting expression of an antigen associated with an effector memory T cell and/or an antigen associated with a terminal effector memory T cell.

10. The method according to claim 7, wherein the level of $CD4^+$ effector memory T cells is measured by detecting the marker CD62L, and wherein the biological sample has an increased percentage of $CD62L^-$ $CD4^+$ T cells and/or $CD62L^-$ $CD8^+$ T cells.

11. The method according to claim 7, wherein the level of $CD4^+$ effector memory T cells is measured by detecting the marker CD62L and CD45RA, and wherein the biological sample has an increased percentage of $CD62L^-/CD45RA^-$ $CD4^+$ T cells.

12. The method according to claim 1, wherein the level and/or proliferation of $CD4^+$ and/or $CD8^+$ naïve T cells and/or central memory T cells is measured, and wherein the biological sample has a decreased percentage of $CD4^+$ and/or $CD8^+$ naïve T cells and/or central memory T cells.

13. The method according to claim 1, wherein the level and/or proliferation of $CD4^+$ and/or $CD8^+$ central memory T cells is measured, and wherein the biological sample has a decreased percentage of $CD4^+$ and/or $CD8^+$ central memory T cells.

14. The method according to claim 12, wherein the level of $CD4^+$ and/or $CD8^+$ naïve T cells and/or central memory T cells is measured by detecting expression of an antigen associated with a naïve T cell and/or an antigen associated with a central memory T cell.

15. The method according to claim 12, wherein the level of $CD4^+$ central memory T cells and/or $CD8^+$ central memory T cells is measured by detecting the marker CD62L, and wherein the biological sample has a decreased percentage of $CD62L^+$ $CD4^+$ T cells and/or $CD62L^+$ $CD8^+$ T cells.

16. The method according to claim 12, wherein the level of $CD4^+$ central memory T cells and/or $CD8^+$ central memory T cells is measured by detecting the marker CD62L and CD45RA, and wherein the biological sample has a decreased percentage of $CD62L^-/CD45RA^-$ $CD4^+$ T cells and/or $CD62L^-/CD45RA^-$ $CD8^+$ T cells.

17. The method according to claim 1, wherein the biological sample is a blood sample.

18. The method according to claim 8, wherein the level of $CD4^+$ and/or $CD8^+$ effector memory T cells and/or terminal effector memory T cells is measured by detecting expression of an antigen associated with an effector memory T cell and/or an antigen associated with a terminal effector memory T cell.

19. The method according to claim 8, wherein the level of $CD4^+$ effector memory T cells is measured by detecting the marker CD62L, and wherein the biological sample has an increased percentage of $CD62L^-$ $CD4^-$ T cells and/or $CD62L^-$ $CD8^+$ T cells.

20. The method according to claim 8, wherein the level of $CD4^+$ effector memory T cells is measured by detecting the marker CD62L and CD45RA, and wherein the biological sample has an increased percentage of $CD62L^-/CD45RA^-$ $CD4^+$ T cells.

21. The method according to claim 13, wherein the level of $CD4^+$ and/or $CD8^+$ naïve T cells and/or central memory T cells is measured by detecting expression of an antigen associated with a naïve T cell and/or an antigen associated with a central memory T cell.

22. The method according to claim 13, wherein the level of $CD4^+$ central memory T cells and/or $CD8^+$ central memory T cells is measured by detecting the marker CD62L, and wherein the biological sample has a decreased percentage of $CD62L^+$ $CD4^+$ T cells and/or $CD62L^+$ $CD8^+$ T cells.

23. The method according to claim 13, wherein the level of $CD4^+$ central memory T cells and/or $CD8^+$ central memory T cells is measured by detecting the marker CD62L and CD45RA, and wherein the biological sample has a decreased percentage of CD62L⁻/CD45RA⁻ CD4⁺ T cells and/or CD62L⁻/CD45RA⁻ CD8⁺ T cells.

24. The method according to claim 1, further comprising obtaining the biological sample from the patient, wherein the biological sample is a blood sample.

25. The method according to claim 1, wherein the IST is anti-thymocyte globulin (ATG) therapy, cyclosporine A (CyA) therapy, or both ATG and CyA therapy.

26. The method according to claim 1, wherein said measuring comprises flow cytometry.

27. The method according to claim 1, wherein the other moiety is a nucleic acid aptamer.

28. The method according to claim 27, wherein said measuring comprises flow cytometry.

29. The method according to claim 1, wherein said measuring comprises a dot blot, enzyme-linked immunoassay (ELISA), or Western blot.

30. The method according to claim 1, wherein said measuring comprises quantitating the marker protein of the CD4⁺ T cells and/or CD8⁺ T cells by contacting the biological sample with the antibody or antibody fragment that binds specifically to the marker protein.

31. The method according to claim 30, wherein said measuring comprises flow cytometry.

32. The method according to claim 1, wherein the IST comprises administration of anti-thymocyte globulin (ATG), cyclosporine A (CyA), ATG in combination with CyA, anti-IL-2 antibody, anti-CD3, Tacrolimus, interferon, azathioprine, or an alkylating agent.

* * * * *